US011564847B2

(12) United States Patent
Beadle et al.

(10) Patent No.: US 11,564,847 B2
(45) Date of Patent: Jan. 31, 2023

(54) NEGATIVE PRESSURE WOUND TREATMENT APPARATUSES AND METHODS WITH INTEGRATED ELECTRONICS

(71) Applicant: Smith & Nephew PLC, Watford (GB)

(72) Inventors: Victoria Beadle, Hull (GB); Mark Hesketh, Royston (GB); William Kelbie, Iverness (GB); Damyn Musgrave, Cottenham (GB); Joseph William Robinson, Papworth Everard (GB); Daniel Steward, Hull (GB)

(73) Assignee: Smith & Nephew PLC, Watford (GB)

( * ) Notice: Subject to any disclaimer, the term of this patent is extended or adjusted under 35 U.S.C. 154(b) by 284 days.

(21) Appl. No.: 16/338,400

(22) PCT Filed: Sep. 29, 2017

(86) PCT No.: PCT/EP2017/074764
§ 371 (c)(1),
(2) Date: Mar. 29, 2019

(87) PCT Pub. No.: WO2018/060417
PCT Pub. Date: Apr. 5, 2018

(65) Prior Publication Data
US 2020/0022846 A1    Jan. 23, 2020

Related U.S. Application Data

(60) Provisional application No. 62/558,263, filed on Sep. 13, 2017, provisional application No. 62/402,551, filed on Sep. 30, 2016.

(51) Int. Cl.
*A61F 13/02*    (2006.01)
*A61M 1/00*    (2006.01)
(Continued)

(52) U.S. Cl.
CPC ........ *A61F 13/0216* (2013.01); *A61F 13/022* (2013.01); *A61M 1/962* (2021.05);
(Continued)

(58) Field of Classification Search
CPC .......... A61M 1/009; A61M 2205/7518; A61M 1/0052; A61M 1/90; A61M 1/962;
(Continued)

(56) References Cited

U.S. PATENT DOCUMENTS 3,874,387 A    4/1975  Barbieri
4,224,941 A    9/1980  Stivala
(Continued)

FOREIGN PATENT DOCUMENTS

CN    201664463 U    12/2010
DE    19844355 A1    4/2000
(Continued)

OTHER PUBLICATIONS

International Search Report and Written Opinion, re PCT Application No. PCT/EP2017/074764, dated Jan. 2, 2018.
(Continued)

*Primary Examiner* — Jessica Arble
(74) *Attorney, Agent, or Firm* — Knobbe, Martens Olson & Bear LLP

(57) ABSTRACT

Disclosed embodiments relate to apparatuses and methods for wound treatment. In some embodiments, a wound dressing apparatus can comprise a wound contact layer, a spacer layer, an absorbent layer positioned on the spacer layer, an electronics unit comprising a negative pressure source and/or electronic components, wherein the absorbent layer comprises a recess configured to receive the electronics unit and the absorbent layer is configured to be in fluid communication with the electronics unit, and a cover layer configured
(Continued)

to cover and form a seal over the wound contact layer, the spacer layer, the absorbent layer, and the electronics unit.

16 Claims, 21 Drawing Sheets

(51) Int. Cl.
*A61F 13/00* (2006.01)
*F21Y 115/10* (2016.01)

(52) U.S. Cl.
CPC . *A61F 13/0253* (2013.01); *A61F 2013/00174* (2013.01); *F21Y 2115/10* (2016.08)

(58) Field of Classification Search
CPC ............... A61F 13/0216; A61F 13/022; A61F 12/0253; A61F 2013/00174
See application file for complete search history.

(56) References Cited

U.S. PATENT DOCUMENTS

| | | | |
|---|---|---|---|
| 4,398,910 A | 8/1983 | Blake et al. | |
| 4,534,356 A | 8/1985 | Papadakis | |
| 4,569,674 A | 2/1986 | Phillips et al. | |
| 4,624,656 A | 11/1986 | Clark et al. | |
| 4,681,562 A | 7/1987 | Beck et al. | |
| 4,767,943 A | 8/1988 | Adler et al. | |
| 4,979,944 A | 12/1990 | Luzsicza | |
| 5,055,195 A | 10/1991 | Trasch et al. | |
| 5,055,198 A | 10/1991 | Shettigar | |
| 5,056,510 A | 10/1991 | Gilman | |
| 5,152,757 A | 10/1992 | Eriksson | |
| 5,181,905 A | 1/1993 | Flam | |
| 5,266,928 A | 11/1993 | Johnson | |
| D357,743 S | 4/1995 | Bilitz et al. | |
| 5,527,293 A | 6/1996 | Zamierowski | |
| 5,549,584 A | 8/1996 | Gross | |
| 5,636,643 A | 6/1997 | Argenta et al. | |
| 5,643,189 A | 7/1997 | Masini | |
| 5,779,657 A | 7/1998 | Daneshvar | |
| 5,833,646 A | 11/1998 | Masini | |
| 5,902,256 A | 5/1999 | Benaron | |
| 5,964,723 A | 10/1999 | Augustine | |
| 6,071,267 A | 6/2000 | Zamierowski | |
| 6,142,982 A | 11/2000 | Hunt et al. | |
| 6,168,800 B1 | 1/2001 | Dobos et al. | |
| 6,183,438 B1 | 2/2001 | Berguer | |
| 6,225,523 B1 | 5/2001 | Masini | |
| 6,261,276 B1 | 7/2001 | Reitsma | |
| 6,261,283 B1 | 7/2001 | Morgan et al. | |
| 6,377,848 B1 * | 4/2002 | Garde ................. | A61M 31/002 604/20 |
| 6,398,767 B1 | 6/2002 | Fleischmann | |
| 6,458,109 B1 | 10/2002 | Henley et al. | |
| 6,471,982 B1 | 10/2002 | Lydon et al. | |
| 6,599,262 B1 | 7/2003 | Masini | |
| 6,607,495 B1 | 8/2003 | Skalak et al. | |
| 6,685,681 B2 | 2/2004 | Lockwood et al. | |
| 6,787,682 B2 | 9/2004 | Gilman | |
| 6,794,554 B2 | 9/2004 | Sessions et al. | |
| 6,800,074 B2 | 10/2004 | Henley et al. | |
| 6,855,135 B2 | 2/2005 | Lockwood et al. | |
| 6,942,633 B2 | 9/2005 | Odland | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,022,113 B2 | 4/2006 | Lockwood et al. | |
| 7,067,709 B2 | 6/2006 | Murata et al. | |
| 7,070,584 B2 | 7/2006 | Johnson et al. | |
| 7,087,806 B2 | 8/2006 | Scheinberg et al. | |
| 7,108,683 B2 | 9/2006 | Zamierowski | |
| 7,338,482 B2 | 3/2008 | Lockwood et al. | |
| 7,361,184 B2 | 4/2008 | Joshi | |
| 7,524,315 B2 | 4/2009 | Blott et al. | |
| 7,553,306 B1 | 6/2009 | Hunt et al. | |
| 7,611,500 B1 | 11/2009 | Lina et al. | |
| 7,615,036 B2 | 11/2009 | Joshi et al. | |
| D605,775 S | 12/2009 | Koch et al. | |
| D608,007 S | 1/2010 | Arbesman et al. | |
| 7,645,253 B2 | 1/2010 | Gura et al. | |
| 7,687,678 B2 | 3/2010 | Jacobs | |
| 7,699,823 B2 | 4/2010 | Haggstrom et al. | |
| 7,776,028 B2 | 8/2010 | Miller et al. | |
| D625,422 S | 10/2010 | Arbesman et al. | |
| 7,815,616 B2 | 10/2010 | Boehringer et al. | |
| 7,837,673 B2 | 11/2010 | Vogel | |
| 7,846,141 B2 | 12/2010 | Weston | |
| 7,896,864 B2 | 3/2011 | Lockwood et al. | |
| 7,922,676 B2 | 4/2011 | Daskal et al. | |
| 7,922,703 B2 | 4/2011 | Riesinger | |
| 7,942,866 B2 | 5/2011 | Radl et al. | |
| 7,959,624 B2 | 6/2011 | Riesinger | |
| 7,976,519 B2 | 7/2011 | Bubb et al. | |
| 8,007,257 B2 | 8/2011 | Heaton et al. | |
| 8,007,481 B2 | 8/2011 | Schuessler et al. | |
| 8,062,272 B2 | 11/2011 | Weston | |
| 8,080,702 B2 | 12/2011 | Blott et al. | |
| 8,092,441 B2 | 1/2012 | Sugito | |
| 8,158,844 B2 | 4/2012 | McNeil | |
| 8,167,869 B2 | 5/2012 | Wudyka | |
| 8,212,100 B2 | 7/2012 | Moore | |
| 8,215,929 B2 | 7/2012 | Shen et al. | |
| 8,323,264 B2 | 12/2012 | Weston et al. | |
| 8,371,829 B2 | 2/2013 | Jaeb et al. | |
| 8,372,049 B2 | 2/2013 | Jaeb et al. | |
| 8,372,050 B2 | 2/2013 | Jaeb et al. | |
| 8,404,921 B2 | 3/2013 | Lee et al. | |
| 8,409,160 B2 | 4/2013 | Locke et al. | |
| 8,414,519 B2 | 4/2013 | Hudspeth et al. | |
| 8,419,696 B2 | 4/2013 | Wilkes | |
| 8,425,478 B2 | 4/2013 | Olson | |
| 8,439,894 B1 | 5/2013 | Miller | |
| 8,449,508 B2 | 5/2013 | Coulthard et al. | |
| 8,500,776 B2 | 8/2013 | Ebner | |
| 8,529,548 B2 | 9/2013 | Blott et al. | |
| 8,545,466 B2 | 10/2013 | Andresen et al. | |
| 8,579,872 B2 | 11/2013 | Coulthard et al. | |
| 8,603,074 B2 | 12/2013 | Kagan | |
| 8,604,265 B2 | 12/2013 | Locke et al. | |
| 8,641,691 B2 | 2/2014 | Fink et al. | |
| 8,641,693 B2 | 2/2014 | Locke et al. | |
| 8,702,665 B2 | 4/2014 | Locke et al. | |
| 8,764,732 B2 | 7/2014 | Hartwell | |
| 8,795,257 B2 | 8/2014 | Coulthard et al. | |
| 8,814,842 B2 | 8/2014 | Coulthard et al. | |
| 8,821,458 B2 | 9/2014 | Locke et al. | |
| 8,870,837 B2 | 10/2014 | Locke et al. | |
| 8,961,496 B2 | 2/2015 | Locke et al. | |
| 8,974,429 B2 | 3/2015 | Gordon et al. | |
| 9,061,095 B2 | 6/2015 | Adie et al. | |
| 9,084,845 B2 | 7/2015 | Adie et al. | |
| 9,089,630 B2 | 7/2015 | Perkins et al. | |
| 9,198,802 B2 | 12/2015 | Robinson et al. | |
| 9,259,558 B2 | 2/2016 | Tsai | |
| 9,265,665 B2 | 2/2016 | Robinson et al. | |
| 9,283,118 B2 | 3/2016 | Locke et al. | |
| 9,393,354 B2 | 7/2016 | Freedman et al. | |
| 9,414,968 B2 | 8/2016 | Heagle | |
| 9,421,133 B2 | 8/2016 | Hu et al. | |
| 9,427,505 B2 | 8/2016 | Askem et al. | |
| 9,452,088 B2 | 9/2016 | Shulman et al. | |
| 9,560,975 B2 | 2/2017 | Mei et al. | |
| D787,690 S | 5/2017 | Mackay et al. | |
| 9,737,649 B2 | 8/2017 | Begin et al. | |
| 9,770,368 B2 | 9/2017 | Robinson et al. | |
| 9,814,811 B2 | 11/2017 | Aalders et al. | |
| 9,907,703 B2 | 3/2018 | Allen et al. | |
| 9,925,092 B2 | 3/2018 | Luckemeyer et al. | |
| RE46,778 E | 4/2018 | Peron | |
| 9,956,120 B2 | 5/2018 | Locke | |
| 10,004,914 B2 | 6/2018 | Nettesheim et al. | |
| 10,016,544 B2 | 7/2018 | Coulthard et al. | |
| 10,046,095 B1 | 8/2018 | Middaugh et al. | |

(56) References Cited

U.S. PATENT DOCUMENTS

| | | | |
|---|---|---|---|
| 10,086,117 B2 | 10/2018 | Locke et al. | |
| 2003/0183659 A1* | 10/2003 | Van Zeeland | H01H 13/702 |
| | | | 222/399 |
| 2003/0212357 A1 | 11/2003 | Pace | |
| 2004/0076662 A1 | 4/2004 | Riesinger | |
| 2004/0087884 A1 | 5/2004 | Haddock et al. | |
| 2004/0167482 A1 | 8/2004 | Watson | |
| 2005/0012616 A1 | 1/2005 | Forster et al. | |
| 2005/0045461 A1 | 3/2005 | Sweetland et al. | |
| 2005/0065471 A1 | 3/2005 | Kuntz | |
| 2005/0119737 A1 | 6/2005 | Bene et al. | |
| 2005/0137539 A1 | 6/2005 | Biggie et al. | |
| 2006/0029650 A1 | 2/2006 | Coffey | |
| 2006/0086598 A1 | 4/2006 | Sneek et al. | |
| 2006/0107642 A1 | 5/2006 | Smith et al. | |
| 2006/0259102 A1 | 11/2006 | Slatkine | |
| 2007/0055209 A1 | 3/2007 | Patel et al. | |
| 2007/0066946 A1* | 3/2007 | Haggstrom | A61F 13/00063 |
| | | | 604/313 |
| 2007/0128055 A1 | 6/2007 | Lee | |
| 2007/0179460 A1 | 8/2007 | Adahan | |
| 2007/0225663 A1 | 9/2007 | Watt et al. | |
| 2007/0255187 A1 | 11/2007 | Branch | |
| 2008/0021356 A1 | 1/2008 | Castello Escude | |
| 2008/0051716 A1 | 2/2008 | Stutz | |
| 2009/0012484 A1 | 1/2009 | Nielsen et al. | |
| 2009/0048556 A1 | 2/2009 | Durand | |
| 2010/0022990 A1 | 1/2010 | Karpowicz et al. | |
| 2010/0100160 A1 | 4/2010 | Edman et al. | |
| 2010/0137775 A1 | 6/2010 | Hu et al. | |
| 2010/0160881 A1 | 6/2010 | Lin et al. | |
| 2010/0207768 A1 | 8/2010 | Pidgeon et al. | |
| 2010/0280469 A1 | 11/2010 | Hall et al. | |
| 2010/0292632 A1 | 11/2010 | Mulvihill et al. | |
| 2011/0028918 A1* | 2/2011 | Hartwell | A61F 13/025 |
| | | | 604/319 |
| 2011/0092927 A1 | 4/2011 | Wilkes et al. | |
| 2011/0112492 A1 | 5/2011 | Bharti et al. | |
| 2011/0224631 A1 | 9/2011 | Simmons et al. | |
| 2011/0292623 A1 | 12/2011 | Stanley | |
| 2011/0305736 A1 | 12/2011 | Wieland et al. | |
| 2012/0016323 A1* | 1/2012 | Robinson | A61M 1/0088 |
| | | | 604/319 |
| 2012/0059294 A1 | 3/2012 | Schubert et al. | |
| 2012/0109034 A1 | 5/2012 | Locke et al. | |
| 2012/0109083 A1* | 5/2012 | Coulthard | A61M 1/90 |
| | | | 604/319 |
| 2012/0325215 A1 | 12/2012 | Levenick et al. | |
| 2013/0215638 A1 | 8/2013 | Dabov et al. | |
| 2013/0317406 A1* | 11/2013 | Locke | A61F 13/022 |
| | | | 602/46 |
| 2014/0100536 A1 | 4/2014 | Angel | |
| 2014/0343518 A1 | 11/2014 | Riesinger | |
| 2015/0057625 A1* | 2/2015 | Coulthard | A61F 13/0216 |
| | | | 604/319 |
| 2015/0065965 A1* | 3/2015 | Haggstrom | A61M 1/0088 |
| | | | 604/304 |
| 2015/0174304 A1* | 6/2015 | Askem | A61M 1/732 |
| | | | 604/319 |
| 2015/0182677 A1 | 7/2015 | Collinson et al. | |
| 2015/0202354 A1 | 7/2015 | Wall | |
| 2015/0216733 A1 | 8/2015 | Allen et al. | |
| 2016/0015873 A1 | 1/2016 | Robinson et al. | |
| 2016/0166438 A1 | 6/2016 | Rovaniemi | |
| 2016/0199546 A1 | 7/2016 | Chao | |
| 2016/0242964 A1 | 8/2016 | Rapp et al. | |
| 2016/0270967 A1 | 9/2016 | Hartwell | |
| 2016/0271305 A1 | 9/2016 | Kurihara et al. | |
| 2016/0361473 A1 | 12/2016 | Robinson et al. | |
| 2017/0112974 A1 | 4/2017 | Fujisaki | |
| 2017/0112975 A1 | 4/2017 | Fujisaki | |
| 2017/0127525 A1 | 5/2017 | Schonholz | |
| 2017/0232189 A1 | 8/2017 | Qin et al. | |
| 2017/0296714 A1 | 10/2017 | Locke et al. | |
| 2017/0319761 A1 | 11/2017 | Locke et al. | |
| 2017/0326277 A1 | 11/2017 | Huang | |
| 2017/0368239 A1 | 12/2017 | Askem et al. | |
| 2018/0008760 A1 | 1/2018 | Zilbershlag et al. | |
| 2018/0021178 A1* | 1/2018 | Locke | A61M 1/962 |
| | | | 602/43 |
| 2018/0028728 A1 | 2/2018 | Aarestad et al. | |
| 2018/0104393 A1 | 4/2018 | Wu et al. | |
| 2018/0200414 A1 | 7/2018 | Askem et al. | |
| 2018/0272052 A1 | 9/2018 | Locke et al. | |
| 2018/0318137 A1 | 11/2018 | Donda et al. | |
| 2018/0318165 A1 | 11/2018 | Donda et al. | |
| 2018/0353771 A1 | 12/2018 | Kim et al. | |
| 2019/0021911 A1 | 1/2019 | Askem et al. | |
| 2019/0125943 A1 | 5/2019 | Askem et al. | |
| 2019/0142644 A1 | 5/2019 | Askem et al. | |
| 2019/0143007 A1 | 5/2019 | Askem et al. | |
| 2019/0159938 A1 | 5/2019 | Askem et al. | |
| 2019/0192350 A1 | 6/2019 | Gowans et al. | |
| 2019/0298580 A1* | 10/2019 | Hall | A61F 13/0223 |
| 2021/0001022 A1 | 1/2021 | Lin | |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2326295 A1 | 6/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 2659915 A1 | 11/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |

(56) References Cited

FOREIGN PATENT DOCUMENTS

| | | |
|---|---|---|
| EP | 2829287 A1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 2249761 B1 | 4/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 2632613 B1 | 8/2017 |
| EP | 2781208 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 2687241 B2 | 11/2018 |
| EP | 2687243 B2 | 11/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2939320 A1 | 6/2010 |
| GB | 2511523 A | 9/2014 |
| JP | H04354722 A | 12/1992 |
| RU | 131622 U1 | 8/2013 |
| WO | WO-2009098696 A2 | 8/2009 |
| WO | WO-2009120951 A2 | 10/2009 |
| WO | WO-2011130570 A1 | 10/2011 |
| WO | WO-2011135285 A1 | 11/2011 |
| WO | WO-2011144888 A1 | 11/2011 |
| WO | WO 2013/136181 | 9/2013 |
| WO | WO-2014099709 A1 | 6/2014 |
| WO | WO-2015116823 A1 | 8/2015 |
| WO | WO-2016126560 A1 | 8/2016 |
| WO | WO 2016/174048 | 11/2016 |
| WO | WO-2017079174 A1 | 5/2017 |
| WO | WO-2017196888 A1 | 11/2017 |
| WO | WO-2018056060 A1 | 3/2018 |
| WO | WO 2018/060412 | 4/2018 |
| WO | WO 2018/060417 | 4/2018 |
| WO | WO-2018115461 A1 | 6/2018 |
| WO | WO-2018156730 A1 | 8/2018 |
| WO | WO-2018158250 A1 | 9/2018 |
| WO | WO-2018162613 A1 | 9/2018 |
| WO | WO-2018164803 A1 | 9/2018 |
| WO | WO-2018185138 A1 | 10/2018 |
| WO | WO-2018192978 A1 | 10/2018 |
| WO | WO-2018206420 A1 | 11/2018 |
| WO | WO-2019053101 A1 | 3/2019 |
| WO | WO-2019053106 A1 | 3/2019 |

OTHER PUBLICATIONS

International Preliminary Report on Patentability for Application No. PCT/EP2017/074755, dated Apr. 11, 2019, 10 pages.
International Preliminary Report on Patentability for Application No. PCT/EP2017/074764, dated Apr. 11, 2019, 9 pages.
International Search Report and Written Opinion for Application No. PCT/EP2017/074755, dated Jan. 2, 2018, 12 pages.

* cited by examiner

NEGATIVE PRESSURE WOUND TREATMENT APPARATUSES AND METHODS WITH INTEGRATED ELECTRONICS

CROSS-REFERENCE TO RELATED APPLICATIONS

This application is a U.S. national stage application of International Patent Application No. PCT/EP2017/074764, filed on Sep. 29, 2017, which claims priority to U.S. Provisional Application No. 62/558263, filed Sep. 13, 2017, U.S. Provisional Application No. 62/402551, filed Sep. 30, 2016.

BACKGROUND

Technical Field

Embodiments described herein relate to apparatuses, systems, and methods the treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Prior art dressings for use in negative pressure such as those described above have included a negative pressure source located in a remote location from the wound dressing. Negative pressure sources located remote from the wound dressing have to be held by or attached to the user or other pump support mechanism. Additionally, a tubing or connector is required to connect the remote negative pressure source to the wound dressing. The remote pump and tubing can be cumbersome and difficult to hide in or attach to patient clothing. Depending on the location of the wound dressing, it can be difficult to comfortably and conveniently position the remote pump and tubing. When used, wound exudate may soak into the dressing, and the moisture from the wound has made it difficult to incorporate electronic components into the dressing.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein. In some embodiments, a negative pressure source is incorporated into a wound dressing apparatus so that the wound dressing and the negative pressure source are part of an integral or integrated wound dressing structure that applies the wound dressing and the negative pressure source simultaneously to a patient's wound. The negative pressure source and/or electronic components may be positioned between a wound contact layer and a cover layer of the wound dressing. An electronics assembly can be incorporated into the absorbent material of the dressing to prevent pooling of wound exudate and maintain conformability of the dressing. These and other embodiments as described herein are directed to overcoming particular challenges involved with incorporating a negative pressure source and/or electronic components into a wound dressing.

According to one embodiment, a wound dressing apparatus can comprise a wound contact layer, the wound contact layer can comprise a proximal wound-facing face and a distal face, wherein the proximal wound-facing face is configured to be positioned in contact with a wound, a spacer layer comprising a proximal wound-facing face and a distal face, the spacer layer positioned over the distal face of the wound contact layer, an absorbent layer positioned on the distal face of the spacer layer, an electronics unit comprising a negative pressure source and/or electronic components, wherein the absorbent layer comprises a recess configured to receive the electronics unit and the absorbent layer is configured to be in fluid communication with the electronics unit and a cover layer configured to cover and form a seal over the wound contact layer, the spacer layer, the absorbent layer, and the electronics unit.

The wound dressing apparatus of the preceding paragraph or in other embodiments can include one or more of the following features. The electronic components can comprise one or more of a power source, a flexible circuit board, a sensor, a switch, and/or a light or LED indicator. The wound dressing further can comprise a negative pressure source inlet protection mechanism and a negative pressure source outlet or exhaust. The negative pressure source outlet or exhaust can comprises an antibacterial membrane and/or a non-return valve. The cover layer can comprise an aperture over the outlet or exhaust. The negative pressure source inlet protection mechanism can comprise a hydrophobic material configured to prevent fluid from entering the negative pressure source.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

DETAILED DESCRIPTION

Figure 1A:
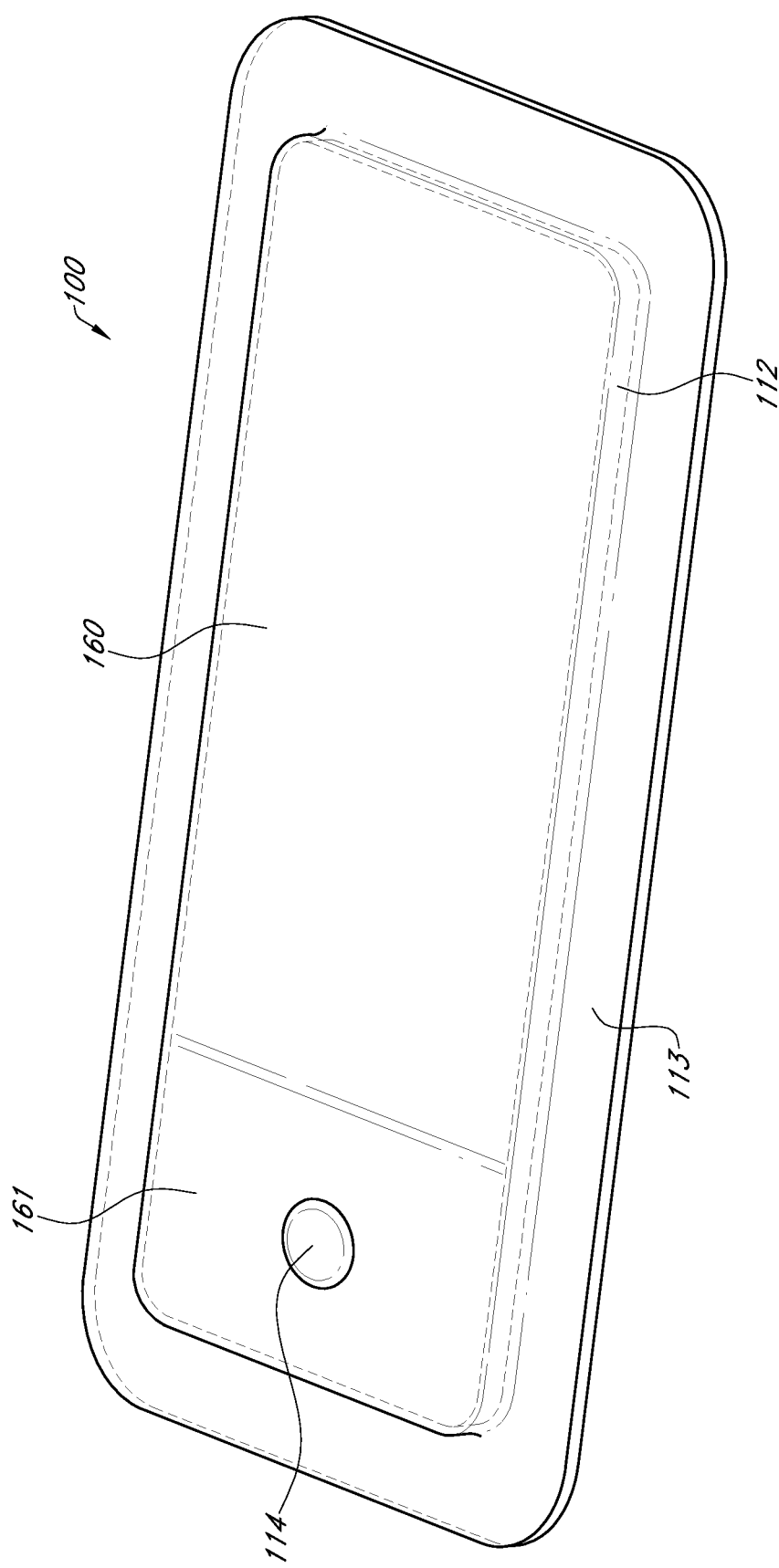
FIG. 1A-1C illustrates a wound dressing apparatus incorporating the pump and/or other electronic components within the wound dressing and offset from the absorbent layer.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated by reference in its entirety herein, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in International Application No. PCT/IB2013/001469, filed May 22, 2013, titled "APPARATUSES AND METHODS FOR NEGATIVE PRES- SURE WOUND THERAPY," published as WO 2013/175306 on Nov. 28, 2013, U.S. patent application Ser. No. 14/418874, filed Jan. 30, 2015, published as U.S. Publication No. 2015/0216733, published Aug. 6, 2015, titled "WOUND DRESSING AND METHOD OF TREATMENT," U.S. patent application Ser. No. 14/418,908, filed Jan. 30, 2015, published as U.S. Publication No. 2015/0190286, published Jul. 9, 2015, titled "WOUND DRESSING AND METHOD OF TREATMENT," U.S. patent application Ser. No. 14/658,068, filed Mar. 13, 2015, U.S. Application No. 2015/0182677, published Jul. 2, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21 2011, published as U.S. 2011/0282309, titled "WOUND DRESSING AND METHOD OF USE," and which is hereby incorporated by reference in its entirety, including further details relating to embodiments of wound dressings, the wound dressing components and principles, and the materials used for the wound dressings.

Embodiments of the wound dressings, wound treatment apparatuses and methods described herein relating to wound dressings with electronics incorporated into the dressing may also be used in combination or in addition to those described in International Application PCT/EP2017/055225, filed Mar. 6, 2017, titled "WOUND TREATMENT APPARATUSES AND METHODS WITH NEGATIVE PRESSURE SOURCE INTEGRATED INTO WOUND DRESSING," and which is hereby incorporated by reference in its entirety, including further details relating to embodiments of wound dressings, the wound dressing components and principles, and the materials used for the wound dressings.

Figure 1B:
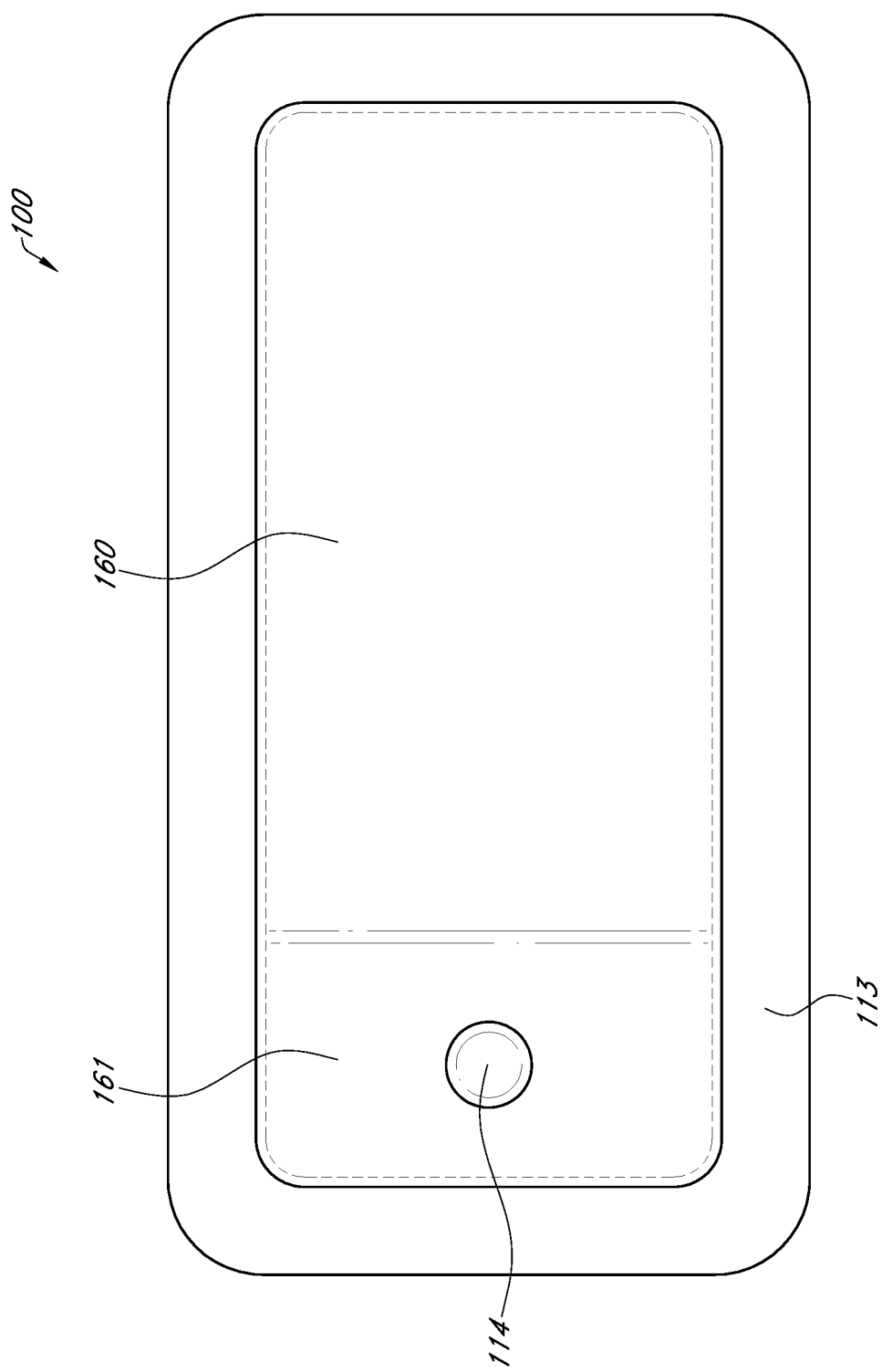
Figure 1C:
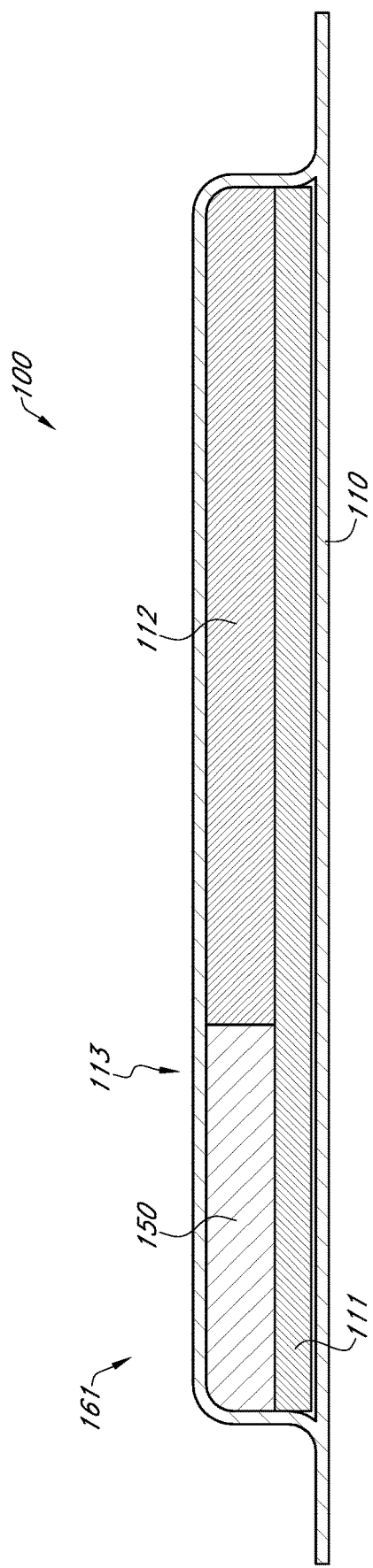

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include various material layers described here and described in further detail in International Application No. PCT/EP2017/055225, filed Mar. 6, 2017, entitled WOUND TREATMENT APPARATUSES AND METHODS WITH NEGATIVE PRESSURE SOURCE INTEGRATED INTO WOUND DRESSING. The material layers can include a wound contact layer, one or more absorbent layers, one or more spacer or transmission layers, and a backing layer or cover layer covering the one or more absorbent and spacer or transmission layers. The wound dressing can be placed over a wound and sealed to the wound with the pump and/or other electronic components contained under the cover layer within the wound dressing. In some embodiments, the dressing can be provided as a single article with all wound dressing elements (including the pump) pre-attached and integrated into a single unit. In some embodiments, a periphery of the wound contact layer can be attached to the periphery of the cover layer enclosing all wound dressing elements as illustrated in FIG. 1A-1C.

In some embodiments, the pump and/or other electronic components can be configured to be positioned adjacent to or next to the absorbent and/or transmission layers so that the pump and/or other electronic components are still part of a single article to be applied to a patient. In some embodiments, with the pump and/or other electronics positioned away from the wound site. FIGS. 1A-1C illustrates a wound dressing incorporating the source of negative pressure and/or other electronic components within the wound dressing. FIGS. 1A-1C illustrates a wound dressing 100 with the pump and/or other electronics positioned away from the wound site. The wound dressing can include an electronics area 161 and an absorbent area 160. The dressing can comprise a wound contact layer 110 (not shown in FIGS. 1A-1B) and a moisture vapor permeable film or cover layer 113 positioned above the contact layer and other layers of the dressing. The wound dressing layers and components of the electronics area as well as the absorbent area can be covered by one continuous cover layer 113 as shown in FIGS. 1A-1C.

The dressing can comprise a wound contact layer 110, a transmission layer 111, an absorbent layer 112, a moisture vapor permeable film or cover layer 113, 113 positioned above the wound contact layer, transmission layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound.

The wound contact layer 110 can be a polyurethane layer or polyethylene layer or other flexible layer which is perforated, for example via a hot pin process, laser ablation process, ultrasound process or in some other way or otherwise made permeable to liquid and gas. The wound contact layer 110 has a lower surface and an upper surface. The perforations preferably comprise through holes in the wound contact layer 110 which enable fluid to flow through the layer 110. The wound contact layer 110 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 110 may help maintain the integrity of the entire dressing 100 while also creating an air tight seal around the absorbent pad in order to maintain negative pressure at the wound.

Some embodiments of the wound contact layer 110 may also act as a carrier for an optional lower and upper adhesive layer (not shown). For example, a lower pressure sensitive adhesive may be provided on the lower surface of the wound dressing 100 whilst an upper pressure sensitive adhesive layer may be provided on the upper surface of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized it may be helpful to adhere the wound dressing 100 to the skin around a wound site. In some embodiments, the wound contact layer may comprise perforated polyurethane film The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 111 of porous or transmission material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. In particular, the transmission layer 111 preferably ensures that an open air channel can be maintained to communicate negative pressure over the wound area even when the absorbent layer has absorbed substantial amounts of exudates. The layer 111 should preferably remain open under the typical pressures that will be applied during negative pressure wound therapy as described above, so that the whole wound site sees an equalized negative pressure. The layer 111 may be formed of a material having a three dimensional structure. For example, a knitted or woven spacer fabric (for example Baltex 7970 weft knitted polyester) or a non-woven fabric could be used.

The transmission layer assists in distributing negative pressure over the wound site and facilitating transport of wound exudate and fluids into the wound dressing. In some embodiments, the transmission layer can be formed at least partially from a three dimensional (3D) fabric.

In some embodiments, the transmission layer 111 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 112 helps lock the liquid away or itself wicks the liquid onwards towards the cover layer 113 where it can be transpired.

Preferably, to improve the liquid flow across the transmission layer 111 (that is to say perpendicular to the channel region formed between the top and bottom spacer layers), the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Further, an absorbent layer (such as layer 112) for absorbing and retaining exudate aspirated from the wound can be utilized. In some embodiments, a superabsorbent material can be used in the absorbent layer 112. In some embodiments, the absorbent includes a shaped form of a superabsorber layer.

A layer 112 of absorbent material is provided above the transmission layer 111. The absorbent material, which comprise a foam or non-woven natural or synthetic material, and which may optionally comprise a super-absorbent material, forms a reservoir for fluid, particularly liquid, removed from the wound site. In some embodiments, the layer 111 may also aid in drawing fluids towards the cover layer 113.

The material of the absorbent layer 112 may also prevent liquid collected in the wound dressing from flowing freely within the dressing, and preferably acts so as to contain any liquid collected within the dressing. The absorbent layer 112 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 112 may typically be manufactured from ALLEVYN™ foam, Freudenberg 114-224-4 or ChemPosite™ 11C-450. In some embodiments, the absorbent layer 112 may comprise a composite comprising superabsorbent powder, fibrous material such as cellulose, and bonding fibers. In a preferred embodiment, the composite is an airlaid, thermally-bonded composite.

In some embodiments, the absorbent layer 112 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

The wound dressing layers of the electronics area and the absorbent layer can be covered by one continuous cover layer or backing layer 113. As used herein, the terms cover layer and/or backing layer can be used interchangeably to refer to the layer of material in the dressing configured to cover the underlying dressing layers and seal to the wound contact layer and/or the skin surrounding the wound. In some embodiments, the cover layer can include a moisture vapor permeable material that prevents liquid exudate removed from the wound and other liquids from passing through, while allowing gases through.

The cover layer 113 is preferably gas impermeable, but moisture vapor permeable, and can extend across the width of the wound dressing 100. The cover layer 113, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer 113 and a wound site where a negative pressure can be established. The cover layer 113 is preferably sealed to the wound contact layer 110 in a border region around the circumference of the dressing, ensuring that no air is drawn in through the border area, for example via adhesive or welding techniques. The cover layer 113 protects the wound from external bacterial contamination (bacterial barrier) and allows liquid from wound exudates to be transferred through the layer and evaporated from the film outer surface. The cover layer 113 preferably comprises two layers; a polyurethane film and an adhesive pattern spread onto the film The polyurethane film is preferably moisture vapor permeable and may be manufactured from a material that has an increased water transmission rate when wet. In some embodiments, the moisture vapor permeability of the cover layer increases when the cover layer becomes wet. The moisture vapor permeability of the wet cover layer may be up to about ten times more than the moisture vapor permeability of the dry cover layer.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch 114 as shown in FIGS. 1A-1B. The button or switch 114 can be used for operating the pump (e.g., turning the pump on/off).

The absorbent area 160 can include an absorbent material 112 and can be positioned over the wound site. The electronics area 161 can be positioned away from the wound site, such as by being located off to the side from the absorbent area 160. The electronics area 161 can be positioned adjacent to and in fluid communication with the absorbent area 160 as shown in FIGS. 1A-1C. In some embodiments, each of the electronics area 161 and absorbent area 160 may be rectangular in shape and positioned adjacent to one another. In some embodiments, the electronics unit can be within absorbent material in the electronics area 160 of the dressing as described herein. As illustrated in FIG. 1C, the electronics unit 150 can be positioned within an absorbent material 112 but off to the side of the absorbent area.

In some embodiments, additional layers of dressing material can be included in the electronics area 161, the absorbent area 160, or both areas. In some embodiments, the dressing can comprise one or more transmission layers and/or one or more absorbent layer positioned above the wound contact layer 110 and below the cover layer 113 of the dressing.

In some embodiments, the electronics area 161 of the dressing can comprise electronic components 150. In some embodiments, the electronics area 161 of the dressing can comprise a plurality of layers of transmission material and/or absorbent material and electronic components 150 can be embedded within the plurality of layers of transmission material and/or absorbent material. The layers of transmission or absorbent material can have recesses or cut outs to embed the electronic components 150 within whilst providing structure to prevent collapse. The electronic components 150 can include a pump, power source, controller, and/or an electronics package.

A pump exhaust can be provided to exhaust air from the pump to the outside of the dressing. The pump exhaust can be in communication with the electronics area 161 and the outside of the dressing.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound. Additionally, the layers can have a proximal wound-facing face referring to a side or face of the layer closest to the skin or wound and a distal face referring to a side or face of the layer furthest from the skin or wound.

FIG. 1A-1C illustrates a wound dressing apparatus incorporating the pump and/or other electronic components within the wound dressing and offset from the absorbent layer. In some embodiments, as shown in FIG. 1C, the absorbent area 160 comprises a transmission layer 111 positioned above the wound contact layer 110. An absorbent layer 112 can be provided above the transmission layer 111. In some embodiments, the electronics area 161 can include an electronics unit (shown in FIGS. 2A-2C). In some embodiments, the electronics unit is provided directly over the wound contact layer. In other embodiments, the electronics unit can be placed above a layer of wicking material, absorbent material, or transmission material that sits above the wound contact layer 110 of the dressing. For example, as shown in FIG. 1C, the electronics unit 150 may be positioned over the transmission layer 111. In some embodiments, the transmission layer 111 can be a single layer of material extending below the electronics unit 150 and the absorbent material 112. Thus, in some embodiments, the transmission layer 111 extends continuously through the absorbent area 160 and the electronics area 161. In alternative embodiments, the transmission layer below the electronics unit can be a different transmission layer than the transmission layer below the absorbent material 112. The transmission layer 111, absorbent material 112, and electronics unit 150 can be covered with a cover layer 113 that seals to a perimeter of the wound contact layer 110 as shown in FIGS. 1A-1C.

The electronics area 161 can include an electronics unit 150 positioned below the cover layer 113 of the dressing. In some embodiments, the electronics unit can be surrounded by a material to enclose or encapsulate a negative pressure source and electronics components by surrounding the electronics. In some embodiments, this material can be a casing. In some embodiments, the electronics unit can be encapsulated or surrounded by a protective coating, for example, a hydrophobic coating as described herein. The electronics unit can be in contact with the dressing layers in the absorbent area 160 and covered by the cover layer 113. As used herein, the electronics unit includes a lower or wound facing surface that is closest to the wound and an opposite, upper surface, furthest from the wound when the wound dressing is placed over a wound.

Figure 2A:
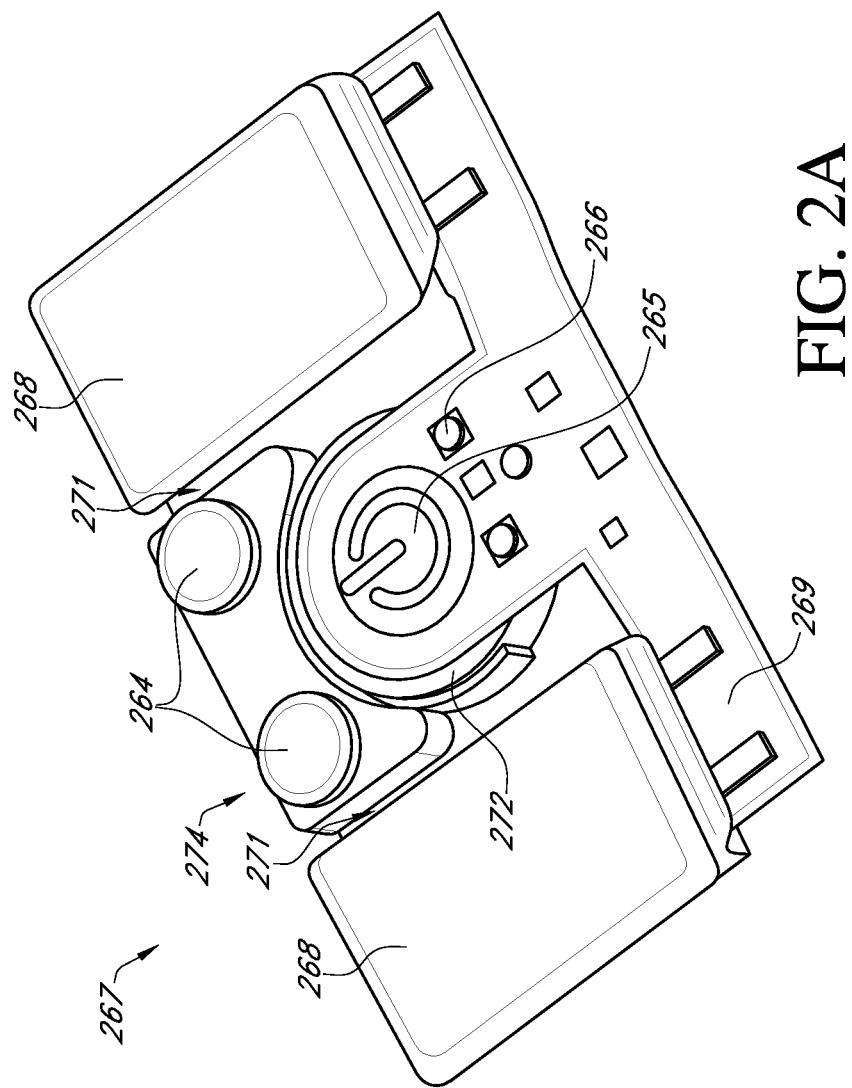
FIG. 2A illustrate an embodiment of the electronics unit.
Figure 2C:
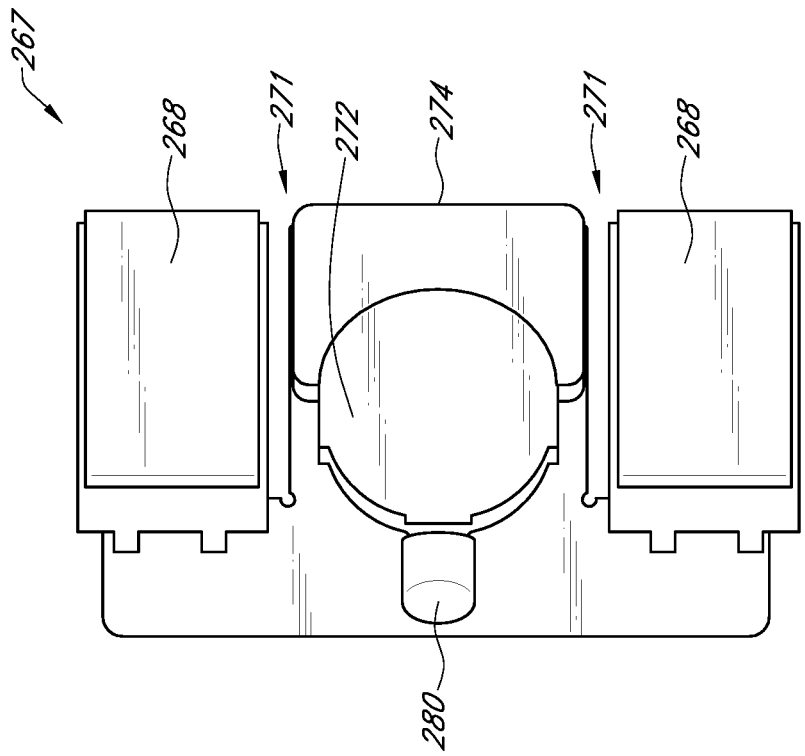
FIGS. 2B-2C illustrate embodiments of the pump and electronics unit.
Figure 2B:
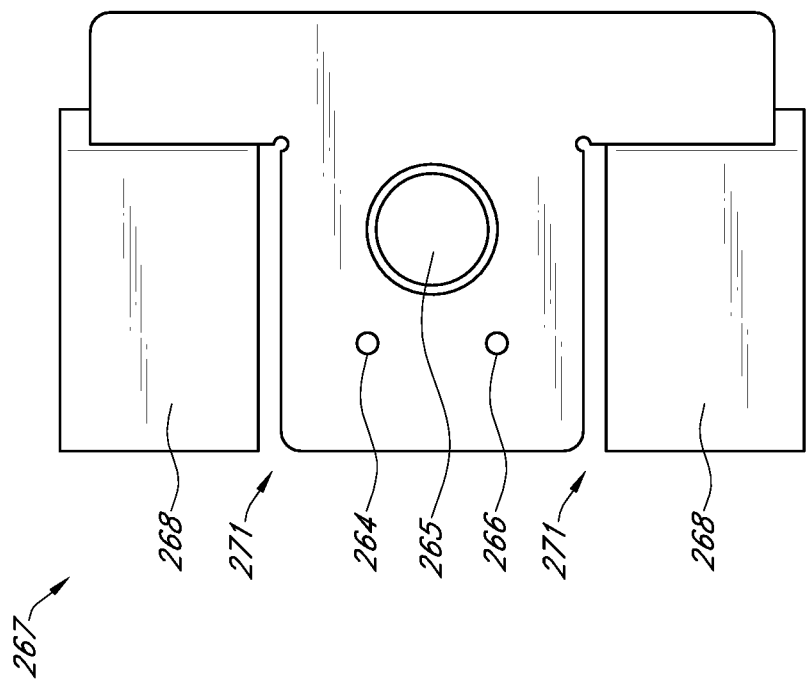

FIG. 2A illustrate an embodiment of the electronics unit 267. FIG. 2A illustrates an embodiment of a pump and electronics unit 267 that can be incorporated into a wound dressing. The electronics unit 267 of FIG. 2A is shown without an electronics casing or other dressing material. FIGS. 2B-2C illustrate embodiments of the pump and electronics unit 267. FIG. 2B illustrates the top view of the electronics unit. FIG. 2C illustrates a bottom or wound facing surface of the electronics unit.

As illustrated in FIG. 2A-2B, the electronics unit 267 can include single button 265 on the upper surface of the unit. The single button 265 can be used as an on/off button or switch to stop and start operation of the pump and/or electronic components. The switch 265 can be a dome type switch configured to sit on the top of the pump. Because the switch is situated within the dressing the cover layer can be easily sealed around or over the switch. In some embodiments, the cover layer can have an opening or hole positioned above the switch. The cover layer can be sealed to the outer perimeter of the switch 265 to maintain negative pressure under the wound cover. The switch can be placed on any surface of the electronics unit and can be in electrical connection with the pump.

The electronics unit 267 can also include one or more vents or exhausts 264 for the pump outlet. However, the vent or exhaust 264 is positioned at the outlet of the pump and extending to the upper surface of the electronics unit. As shown in FIG. 2A, the pump outlet exhaust 264 is attached to the outlet of the pump and provides communication with the top surface of the dressing. In some embodiments, the exhaust 264 can be attached to the outlet end of the pump and can extend out from the pump at a 90-degree angle from the pump orientation to communicate with the top surface of the dressing. The exhaust 264 can include an antibacterial membrane and a non-return valve. The exhausted air from the pump can pass through the pump outlet and exhaust mechanism 274. In some embodiments, the cover layer 113 can include apertures or holes positioned above the exhaust vents 264 and/or membrane. The cover layer 113 can be sealed to the outer perimeter of the exhaust vents 264 to maintain negative pressure under the wound cover 113. In some embodiments, the exhausted air can be exhausted through the gas permeable material or moisture vapor permeable material of the cover layer. In some embodiments, the cover layer does not need to contain apertures or holes over the exhaust and the exhausted air is expelled through the cover layer. In some embodiments, the pump outlet mechanism 274 can be a custom part formed to fit around the pump as shown in FIG. 2A-2C. The electronic unit 267 can include a pump inlet protection mechanism 280 (shown in FIG. 2C) positioned on the portion of the electronic unit closest to the absorbent area and aligned with the inlet of the pump 272. The pump inlet protection mechanism is positioned between the pump inlet and the absorbent area or absorbent layer of the dressing. The pump inlet protection mechanism can be formed of a hydrophobic material to prevent fluid from entering the pump.

In some embodiments, the upper surface of the electronics unit can include one or more indicators 266 for indicating a condition of the pump and/or level of pressure within the dressing. The indicators can be small LED lights or other light source that are visible through the dressing material or through holes in the dressing material above the indicators. The indicators can be green, yellow, red, orange, or any other color. For example, there can be two lights, one green light and one orange light. The green light can indicate the device is working properly and the orange light can indicate that there is some issue with the pump (e.g. dressing leak, saturation level of the dressing, and/or low battery).

FIG. 2A-2C illustrates an embodiment of a pump and electronics unit 267. The electronics unit 267 can include a pump 272 and one or more batteries 268 or other power source to power the pump 272 and other electronics. The pump can operate at about 27 volts or about 30 volts. The two batteries can allow for a more efficient voltage increase (6 volts to 30 volts) than would be possible with a single battery.

The batteries 268 can be in electrical communication with a flexible circuit board 276. In some embodiments, one or more battery connections are connected to a surface of the flexible circuit board 276. In some embodiments, the flexible circuit board can have other electronics incorporated within. For example, the flexible circuit board may have various sensors including, but not limited to, one or more pressure sensors, temperature sensors, optic sensors and/or cameras, and/or saturation indicators.

In such embodiments, the components of the electronics unit 267 may include a protective coating to protect the electronics from the fluid within the dressing. The coating can provide a means of fluid separation between the electronics unit 267 and the absorbent materials of the dressing. The coating can be a hydrophobic coating including, but not limited to, a silicone coating or polyurethane coating. The pump inlet component can be used to protect the pump from fluid on the inlet and the pump outlet mechanism can include a non-return valve that protects fluid from entering the outlet as described in more detail with reference to PCT International Application No. PCT/EP2017/055225, filed Mar. 6, 2017, titled WOUND TREATMENT APPARATUSES AND METHODS WITH NEGATIVE PRESSURE SOURCE INTEGRATED INTO WOUND DRESSING and PCT International Application No. PCT/EP2017/059883, filed Apr. 26, 2017, titled WOUND DRESSINGS AND METHODS OF USE WITH INTEGRATED NEGATIVE PRESSURE SOURCE HAVING A FLUID INGRESS INHIBITION COMPONENT, which are hereby incorporated by reference in their entireties.

The electronics unit 267 includes one or more slits, grooves or recesses 271 in the unit between the pump and the two batteries. The slits, grooves or recesses 271 can allow for the electronics unit 267 to be flexible and conform to the shape of the wound. The unit 267 can have two parallel slits, grooves or recesses 271 forming three segments of the electronics unit 267. The slits, grooves or recesses 271 of the unit 267 create hinge points or gaps that allows for flexibility of the electronics unit at that hinge point. The pump exhaust vents 264, switch 265, and indicator 266 are shown on the top surface surrounded by the electronics unit 267. As illustrated, one embodiment of the electronics unit 267 has two hinge points to separate the unit into three regions or panels, for example one to contain one battery, one to contain the pump, and one to contain another battery. In some embodiments, the slits, grooves or recesses may extend parallel with a longitudinal axis of the dressing that extends along the length of the dressing through the electronics area of the dressing through the absorbent area of the dressing.

Figure 3:
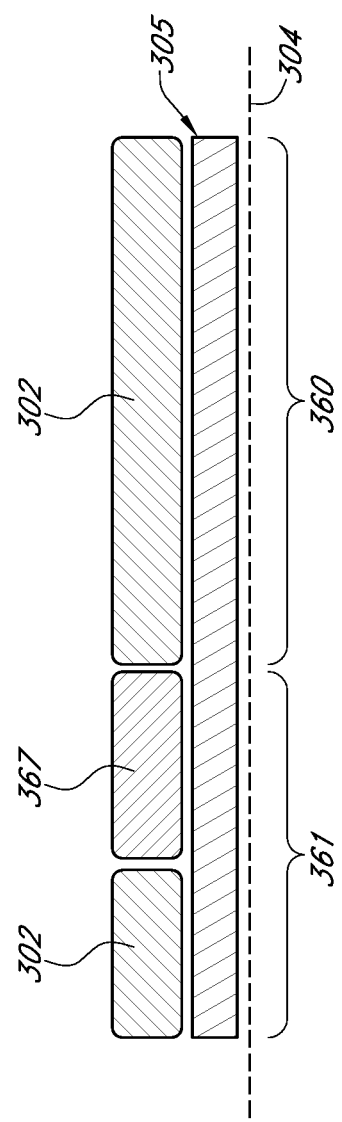
FIG. 3 illustrates an embodiment of a wound dressing incorporating an electronics unit within the dressing.

FIG. 3 illustrates an embodiment of a wound dressing incorporating an electronics unit 367 within the dressing. In some embodiments, the wound dressing can include a wound contact layer 304. The dressing can also include a transmission layer 305 which may be made of a 3D material above the wound contact layer. In some embodiments, the electronics sub assembly or electronics unit 367 can be embedded in an aperture or hole in an absorbent pad 302 towards one end of the dressing, as depicted in FIG. 3. As shown in the cross sectional view of the wound dressing layers in FIG. 3, the absorbent material 302 can be positioned on both sides of the electronic components 367.

In some embodiments, the absorbent components and electronics components can be overlapping but offset. For example, a portion of the electronics area can overlap the absorbent area, for example overlapping the superabsorber layer, but the electronics area is not completely over the absorbent area. Therefore, a portion of the electronics area can be offset from the absorbent area. The dressing layer and electronic components can be enclosed in a wound contact layer 304 positioned below the lower most layer and a cover layer (not shown) positioned above the absorbent layer and electronics. The wound contact layer and cover layer can be sealed at a perimeter enclosing the dressing components. In some embodiments, the cover layer can be in direct physical contact with the absorbent material, and/or the electronics unit. In some embodiments, the cover layer can be sealed to a portion of the electronics unit and/or casing, for example, in areas where holes or apertures are used to accommodate the electronic components (e.g. a switch and/or exhaust).

Figure 4A:
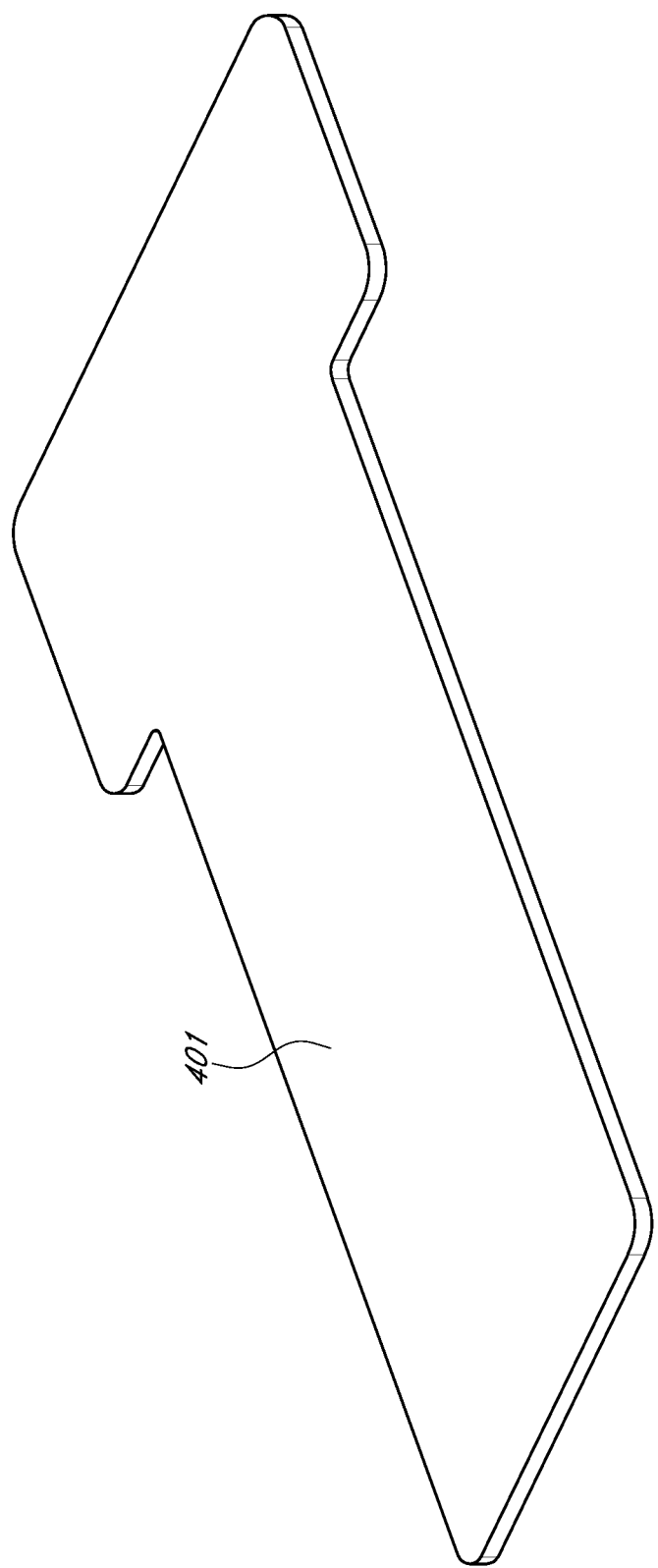
FIGS. 4A-4C illustrate an embodiment of a wound dressing incorporating an electronics unit in the absorbent layer.
Figure 4B:
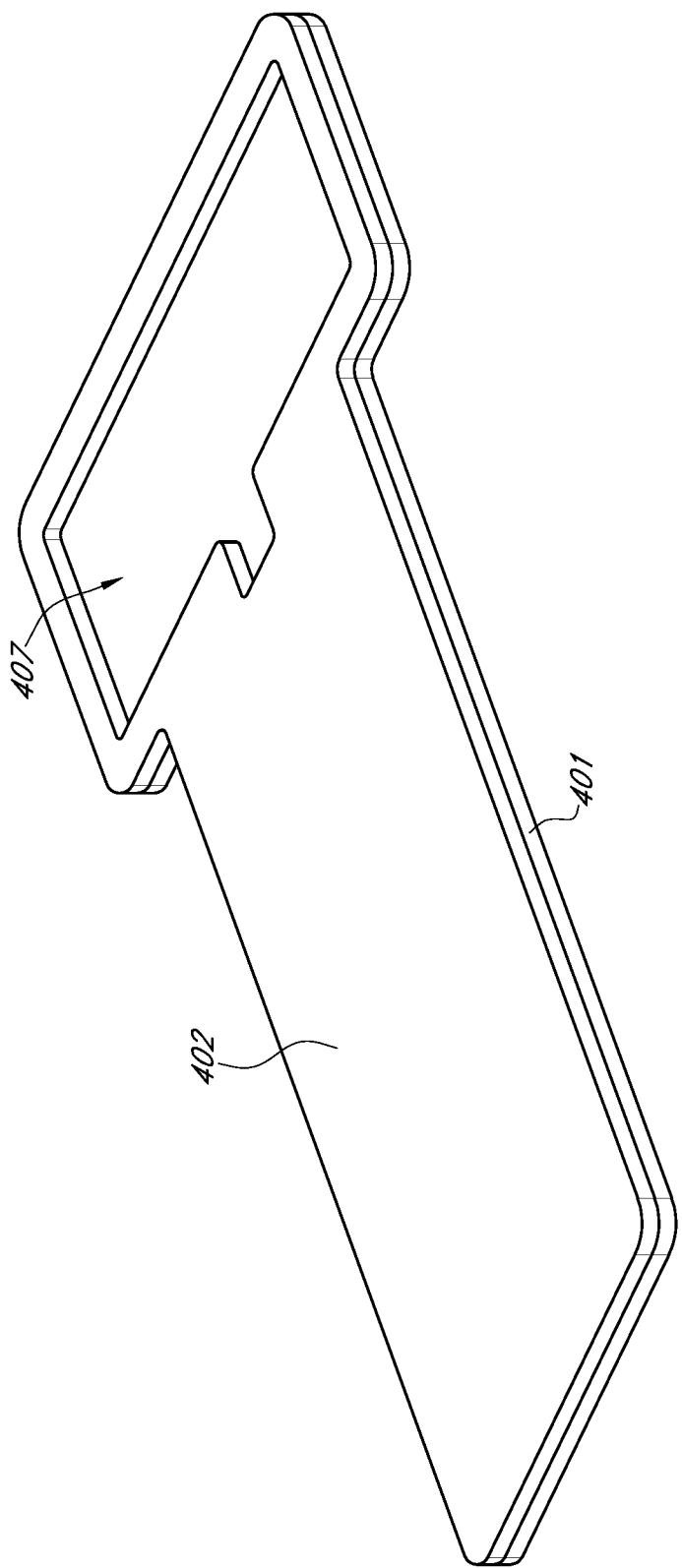
Figure 4C:
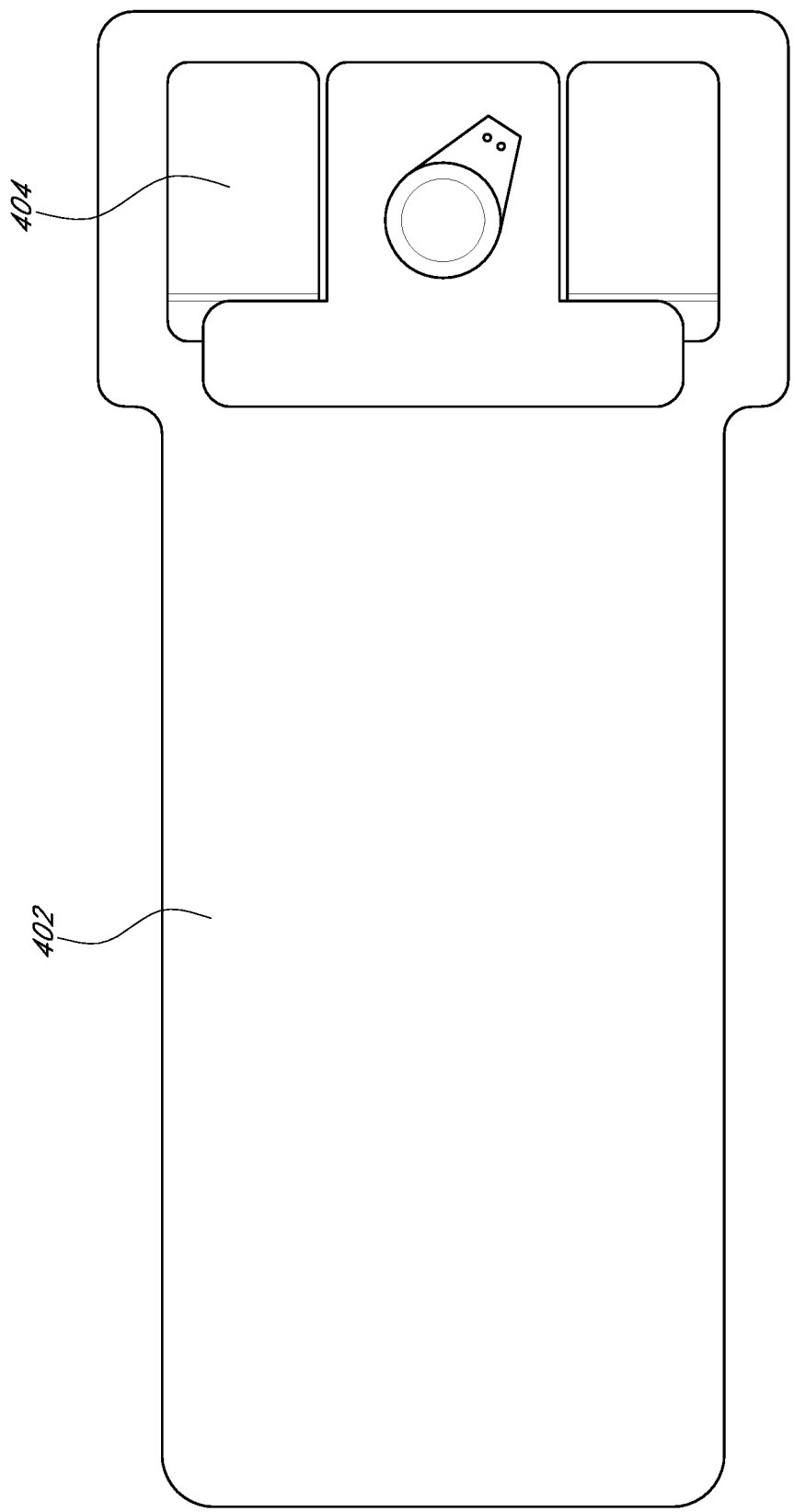

FIGS. 4A-4C illustrate an embodiment of a wound dressing incorporating an electronics unit resting in the absorbent layer. FIG. 4A illustrates a transmission layer 401. FIG. 4B illustrates an absorbent layer 402 provided over the entire length of the transmission layer 401. The absorbent layer has one recess, cutout, or slot 407 in the portion of the absorbent layer 402 located in the electronics area. In FIG. 4B, the transmission layer 401 is visible in the recess 407 of the absorbent layer 402. The recess 407 is spaced and sized to fit the outer perimeter of the batteries and pump assembly of the electronics unit 404 in one recess. In some embodiments, the recess in the absorbent layer can include multiple recesses that are sized to fit individual components of the electronics unit 404, for example, the batteries and pump assembly as illustrated in embodiments described with reference to FIGS. 6, 7A-7C, and 8A-8F. FIG. 4C illustrates the electronics unit 404 positioned within the recess 407 of the absorbent layer 402. The dressing layers and components shown in FIG. 4C can be enclosed in a wound contact layer (not shown) positioned below the transmission layer and a cover layer (not shown) positioned above the absorbent layer and electronics. The wound contact layer and cover layer can be sealed at a perimeter enclosing the dressing components.

Figure 5A:
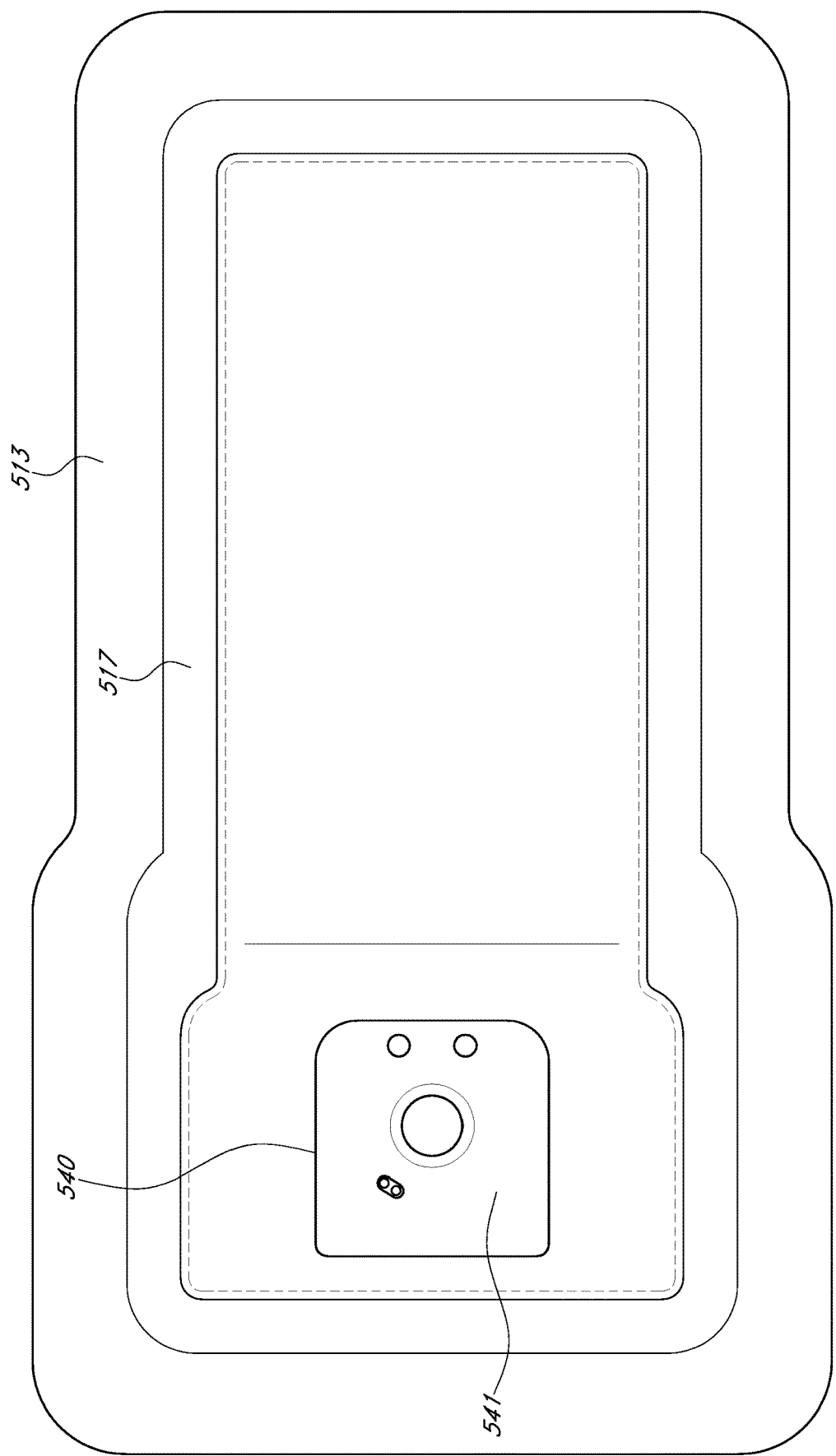
FIGS. 5A-5B illustrate an embodiment of a wound dressing incorporating an electronics unit.
Figure 5B:
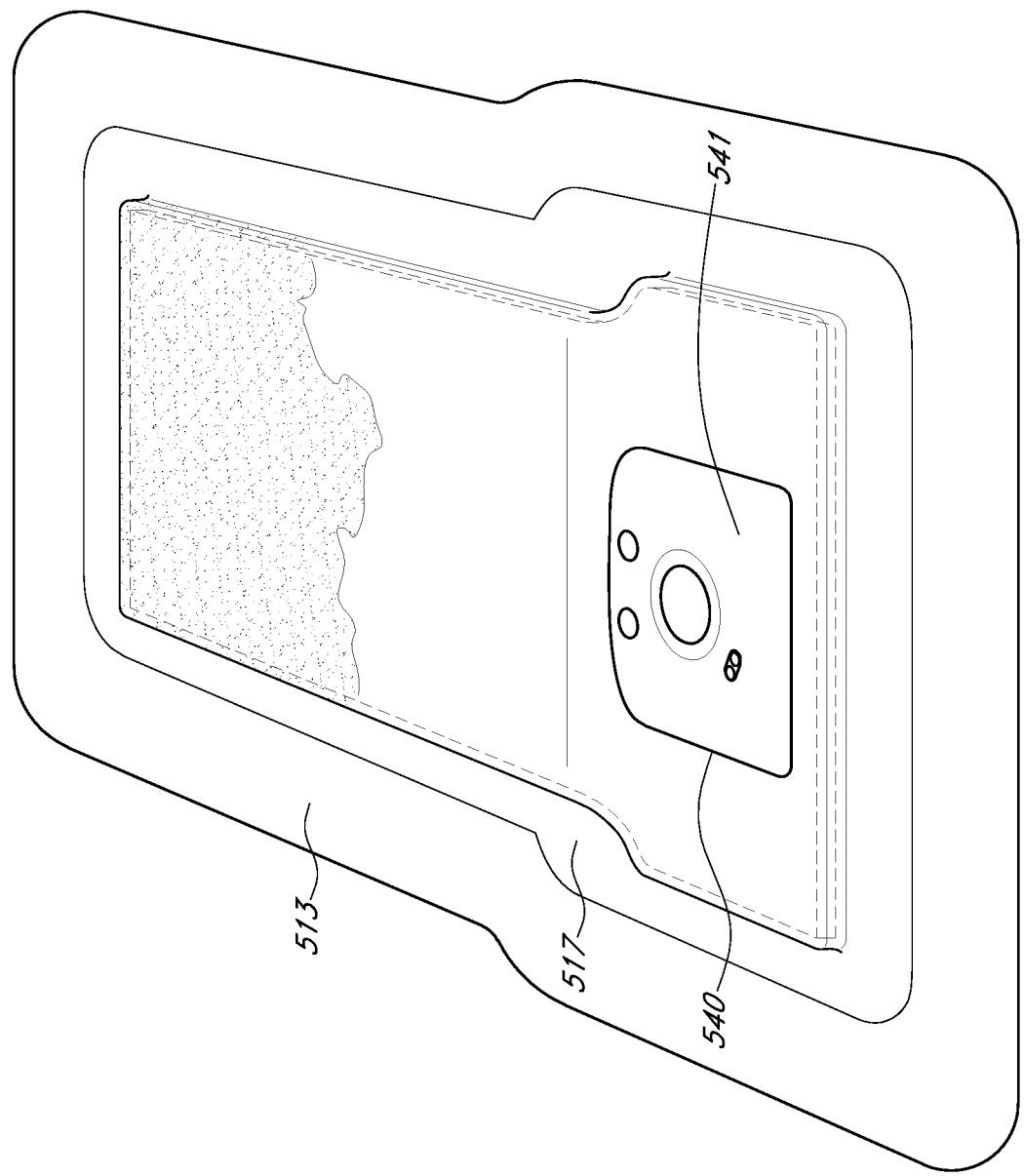

The wound dressing of FIGS. 5A-5B include an overlay layer 517 comprising an additional layer of material positioned above the dressing layers. In some embodiments, the additional layer can include a masking or obscuring layer positioned above the dressing layers. The overlay layer 517 can be positioned above the absorbent layer and electronics and below the cover layer 513. In some embodiments, the overlay layer 517 can include an aperture 540 over a portion of the electronic components to allow the electronic components to be accessible from above the overlay layer. In some embodiments, the overlay layer 517 can be an opaque material that does not allow the wound exudate or other fluid to be visible from a top view of the wound dressing. In some embodiments, the overlay layer can be an absorbent or transmission layer as described herein. In some embodiments, the overlay layer can comprise a conformable material overlaying and overbordering the perimeter of the lower layers of transmission and absorbent materials so as to protect the cover layer from being punctured by the lower layers when sealed over the dressing layers as described in more details below.

The wound dressing can include an electronics label or covering 541 positioned over the aperture 540 in the overlay layer 517. In some embodiments, the label or covering 541 can be positioned under the cover layer 513. In other embodiments, the cover layer 513 can be positioned below the label and can also have an aperture to allow the label or covering 541 to communicate with the underlying electronic components.

FIG. 5B illustrate the wound dressing of FIG. 5A absorbing and retaining fluids while negative pressure is applied to the dressing.

FIGS. 5A-5B illustrate a label or covering 541 that can be positioned over and cover the electronics and an opening 540 in the overlay layer 517

Figure 6:
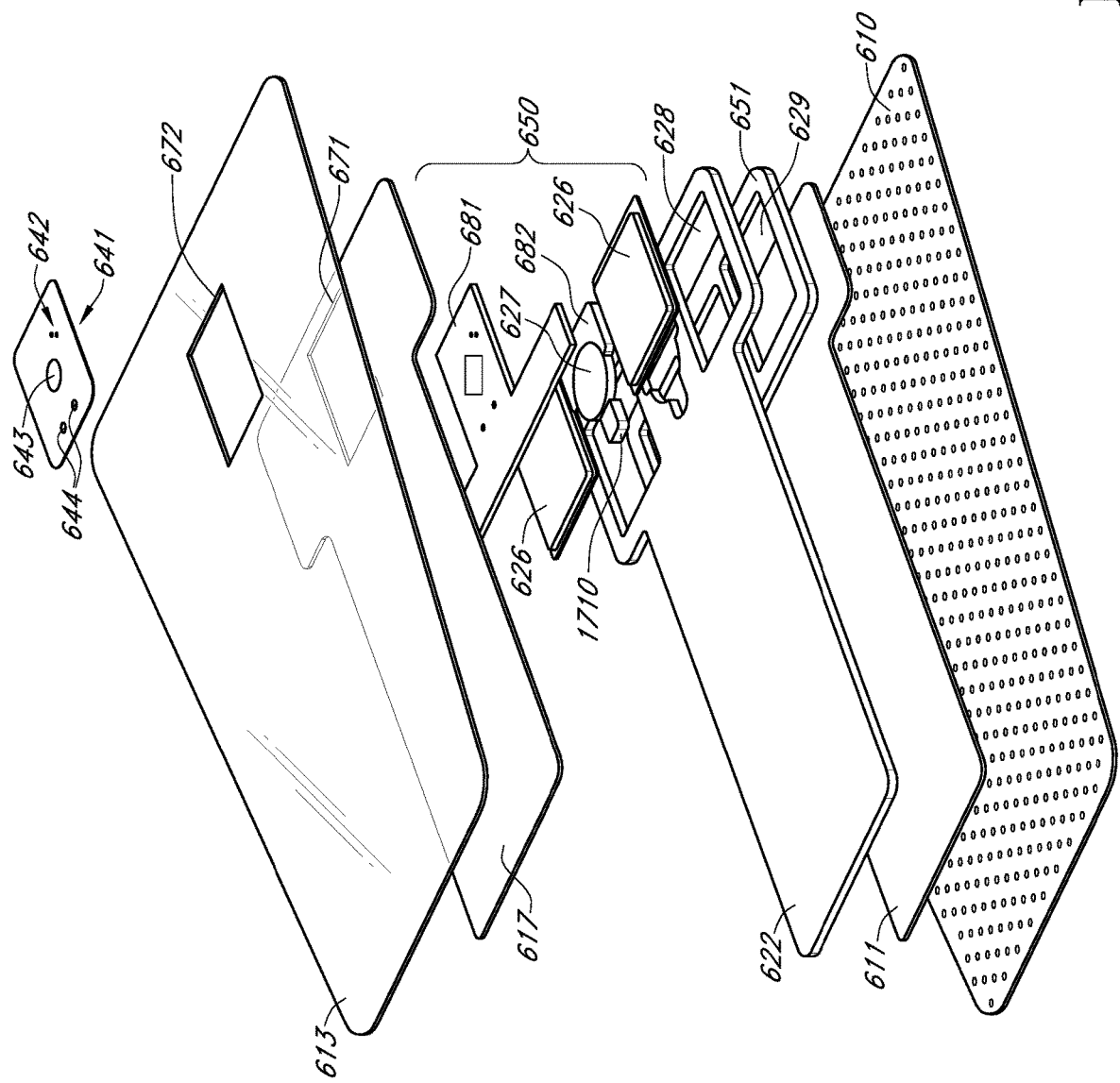
FIG. 6 illustrates an embodiment of wound dressing layers incorporating the electronic components within the wound dressing.

FIG. 6 illustrates an embodiment of wound dressing layers incorporating the electronic components within the wound dressing. FIG. 6 illustrates a wound dressing with a wound contact layer 610 configured to contact the wound. A transmission layer or spacer layer 611 is provided over the wound contact layer 610. The transmission layer 611 can assist in transmitting and distributing negative pressure over the wound site.

A first layer of apertured absorbent material 651 can be provided over the transmission layer 611. The first apertured absorbent layer 651 can include an aperture 629. In some embodiments, the aperture 629 can be sized and shaped to fit the electronics unit 650 therein. The first apertured absorbent layer 651 can be sized and shaped to the size of the electronics area and does not extend into the absorbent area. In some embodiments, the apertures 629 can be shaped and sized to fit the individual components of the electronics unit 650.

A second apertured absorbent layer 622 can be provided over the first absorbent layer 651. In some embodiments, the second absorbent layer 622 include apertures 628. The second absorbent layer 622 can be sized and shaped to the size of the electronics area and absorbent area. In some embodiments, the apertures 628 can be shaped and sized to fit the individual components of the electronics unit 650.

An electronics unit 650 can be positioned in the apertures 628 and 629 of the first and second apertured absorbent material 651 and 622. The electronics unit 650 can include a pump 627, power source 626, and a printed circuit board 681. In some embodiments, the pump 627 can include a pump inlet mechanism 1710 and an outlet mechanism 682. In some embodiments, the printed circuit board 681 can include electronics including but not limited to a switch, sensors, and LEDs as described herein. In some embodiments, the circuit board 681 can include one or more hole to be positioned over one or more exhaust vents (not shown) in the outlet mechanism 682 as described in more detail herein.

An overlay layer 617 can be provided over the electronics components 650 and absorbent layer 622. In some embodiments, the overlay layer 617 can be one or more layers of absorbent and/or transmission material as described herein. In some embodiments, the overlay layer 617 can comprise a conformable material overlaying and overbordering the perimeter of the lower layers of transmission and absorbent materials. In some embodiments, the overlay layer 617 can soften the edges of the wound dressing layers by decreasing the profile around the edges of the dressing layers. In some embodiments, the overlay layer 617 can be provided to protect the cover layer from being punctured by the lower layers when positioned over the dressing layers as described in more details below. The overlay layer 617 can include an aperture 671 to allow access to at least a portion of the electronics unit 650 positioned below.

A cover layer or backing layer 613 can be positioned over the overlay layer 617. In some embodiments, when the overlay layer 617 is not used, the cover layer or backing layer 613 can be provided above absorbent layers 622, and/or electronic components 650. The cover layer 613 can form a seal to the wound contact layer 610 at a perimeter region enclosing the overlay layer 617, absorbent layers 622 and 651, electronic components 650, and the transmission layer 611. In some embodiments, the cover layer 613 can be a flexible sheet of material that forms and molds around the dressing components when they are applied to the wound. In other embodiments, the cover layer 613 can be a material that is preformed or premolded to fit around the dressing components as shown in FIG. 6. As used herein, the terms cover layer and backing layer can be used interchangeably to refer to the layer of material in the dressing configured to cover the layers of the wound dressing.

In some embodiments, the cover layer or backing layer 613 can include an aperture 672. The aperture 672 can be positioned over at least a portion of the aperture 671 in the overlay layer 617 to allow access to at least a portion of the electronics unit 650 positioned below. In some embodiments, the apertures 671 and 672 can allow access to the switch and/or venting holes of the pump exhaust.

A label 641 can be provided over the apertures 671 and 672 and positioned over the exposed portion of the electronic components 650. The label can include the vent holes 642, indicator portions 644, and/or switch cover 643. The indicator portions 644 can include holes or transparent regions 644 for positioning over the one or more indicators or LEDs on the printed circuit board 681 below the label 641. The holes or transparent regions 644 can allow for the indicators or LEDs to be visible through the label 641. In some embodiments, the switch cover 642 can include a dome shaped cover positioned over the switch on the printed circuit board 681. In some embodiments, the label 641 can include embossed features for the switch cover 642. In some embodiments, the embossed features of the switch cover 642 can prevent accidental activation or deactivation of the device. In some embodiments, the switch or switch cover 642 can include a tab on the switch to prevent accidental activation or deactivation. The vent holes 642 of the label can allow exhaust from the pump outlet mechanism to pass through the label and exit the wound dressing to be exhausted to the atmosphere.

In some embodiments, the label can be positioned on top of the cover layer or backing layer 613. The label can be sealed to the top surface of the cover layer. In other embodiments, the label 641 can be positioned above the overlay layer 671 and below the cover layer or backing layer 613. In such embodiments, the cover layer 613 can have one or more apertures over one or more components of the label 641. For example, the cover layer 613 can have apertures over the vent holes 642, indicator portions 644, and/or switch cover 643.

Figure 7B:
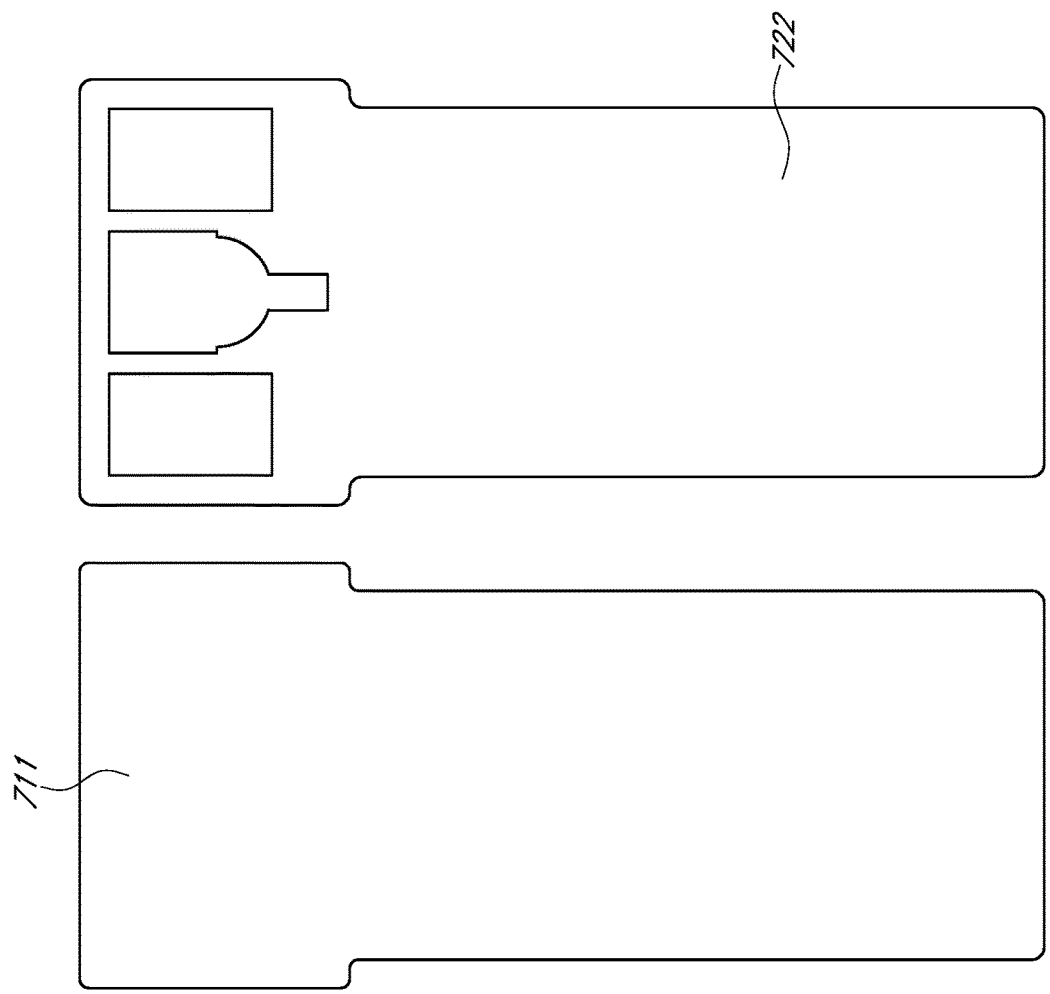
FIGS. 7A-7C illustrates embodiments of individual layers of a wound dressing.
Figure 7A:
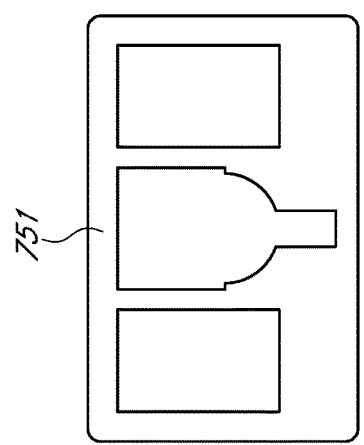
Figure 7C:
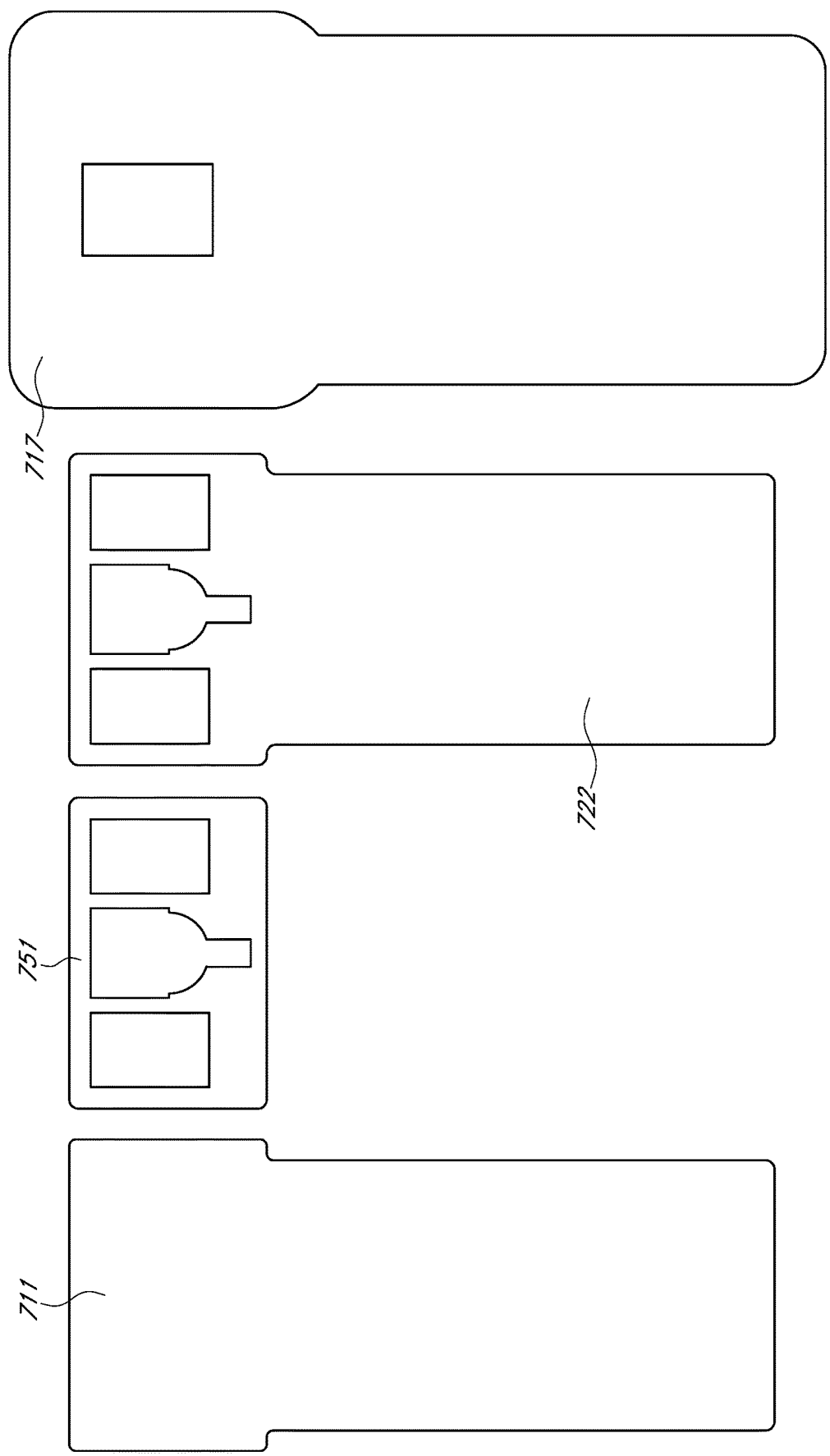

FIGS. 7A-7C illustrates the individual layers of a wound dressing. FIG. 7A illustrates a first apertured absorbent material 751 cut to fit the size and shape of the electronics area.

FIG. 7B illustrates a second apertured absorbent layer 722 and a transmission layer 711. Both the second absorbent layer 722 and transmission layer 711 can be a similar size and shape as shown in FIG. 7B. The first apertured absorbent material 751 can be a smaller apertured absorbent material than the size of the second apertured absorbent layer 722.

FIG. 7C illustrates a transmission layer 711, a first apertured absorbent layer 751, a second apertured absorbent layer 722, and overlay layer 717. As shown in FIG. 7C, the overlay layer 717 can have a larger perimeter size than the other layers of the dressing as to overhang the edges of the other layers of the wound dressing. In some embodiments, the overlay layer 717 can have a smaller thickness than the absorbent layer 722 and transmission layer 711. In other embodiments, the overlay layer 717 can have the same thickness or a greater thickness than the absorbent layer 722 and transmission layer 711.

Figure 8A:
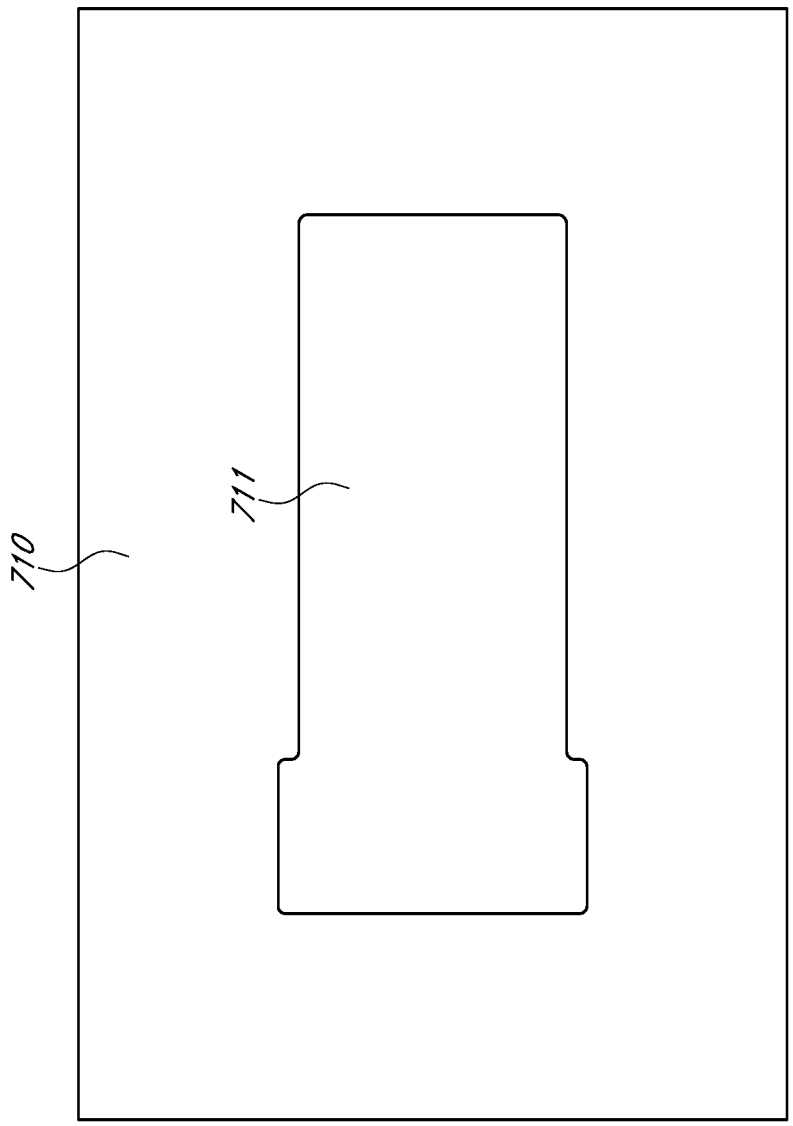
FIGS. 8A-8F illustrates embodiments of layers of the wound dressing incorporating an electronics assembly within the dressing.
Figure 8B:
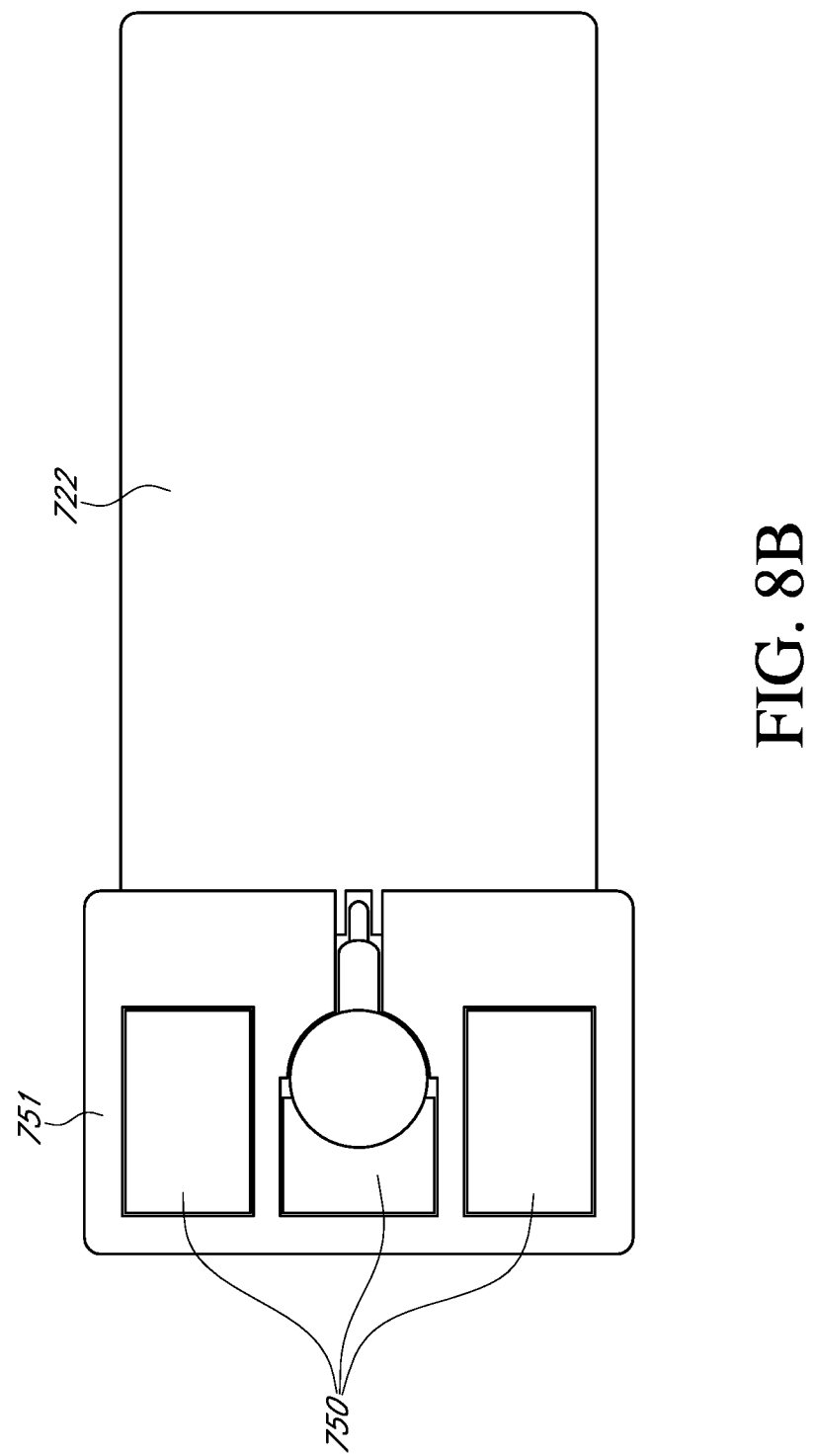
Figure 8C:
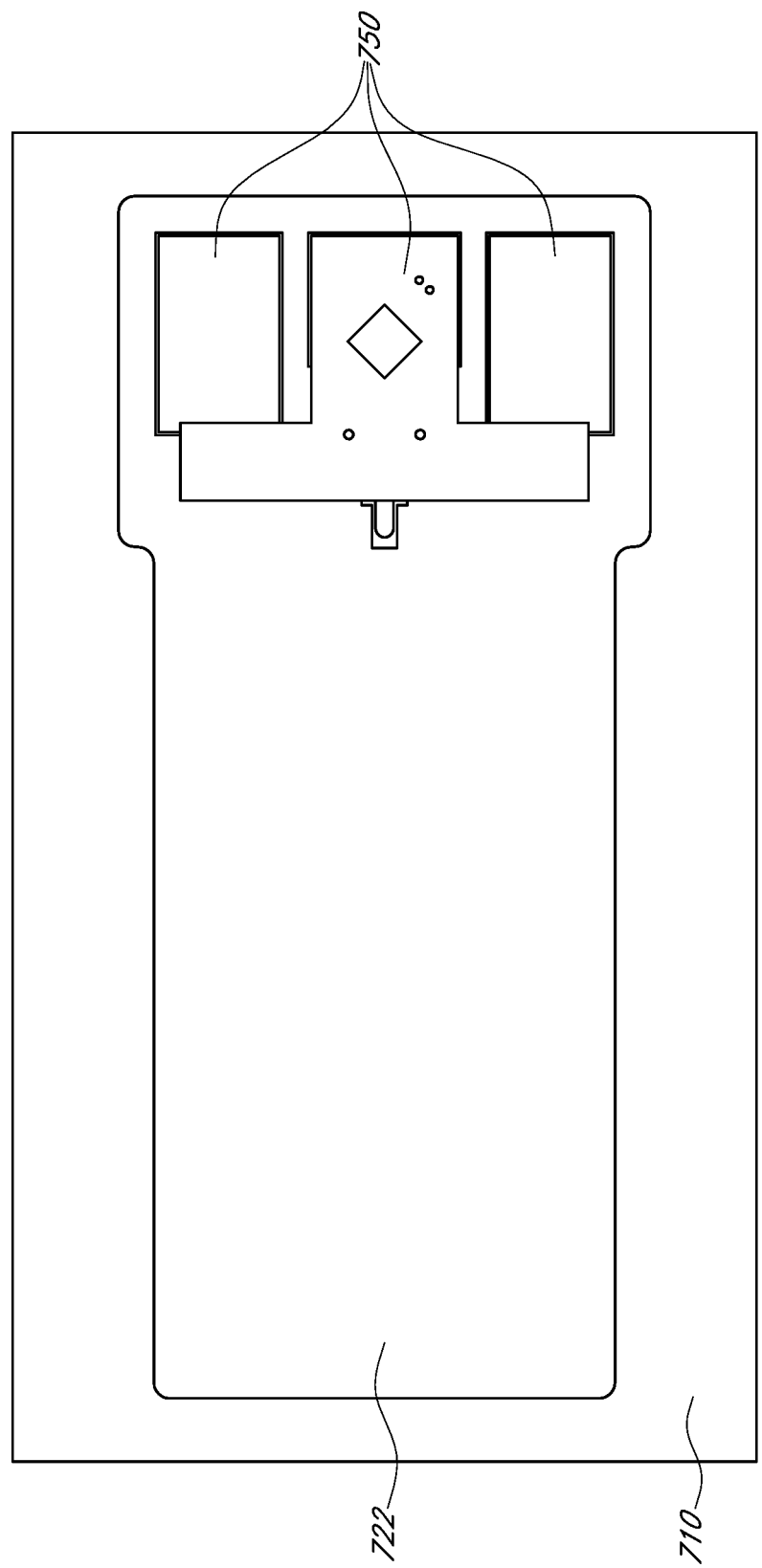

FIGS. 8A-8F illustrates the layers of the wound dressing incorporating an electronics assembly within the dressing. As shown in FIG. 8A, a transmission layer 711 can be placed over a wound contact layer 710. FIG. 8B illustrates a bottom view of components of the wound dressing. FIG. 8B illustrates the bottom view of an electronic unit 750 embedded within the apertures of the first apertured absorbent layer 751 and the second apertured absorbent layer 722. FIG. 8C illustrates a top view of an electronics unit 750 embedded within the apertures of the first apertured absorbent layer 751 (not shown) and the second apertured absorbent layer 722 placed over the transmission layer (not shown) and the wound contact layer 710.

Figure 8D:
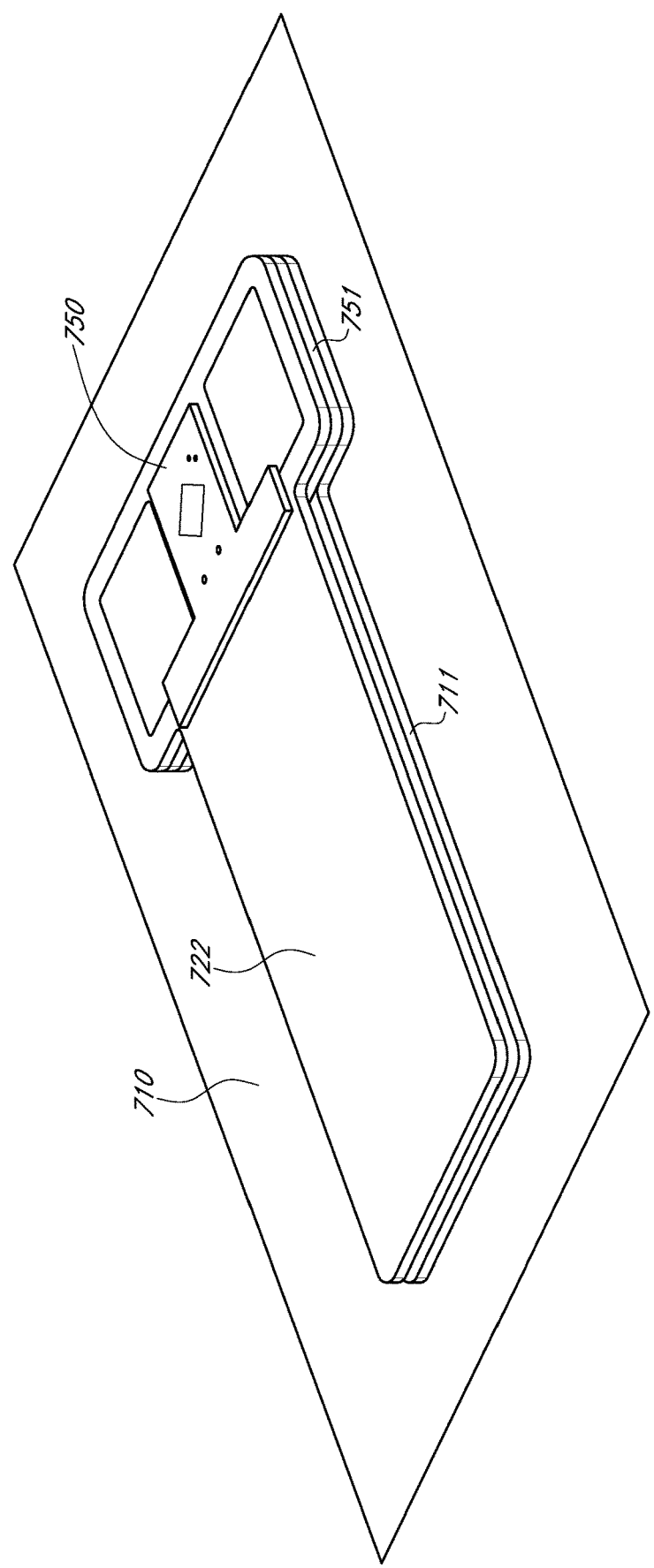

FIG. 8D illustrates the layers of the wound dressing device with the electronics unit 750 embedded within the first apertured absorbent layer 751 and the second apertured absorbent layer 722. The first apertured absorbent layer 751 and the second apertured absorbent layer 722 can be placed over the transmission layer 711 and the wound contact layer 710.

Figure 8E:
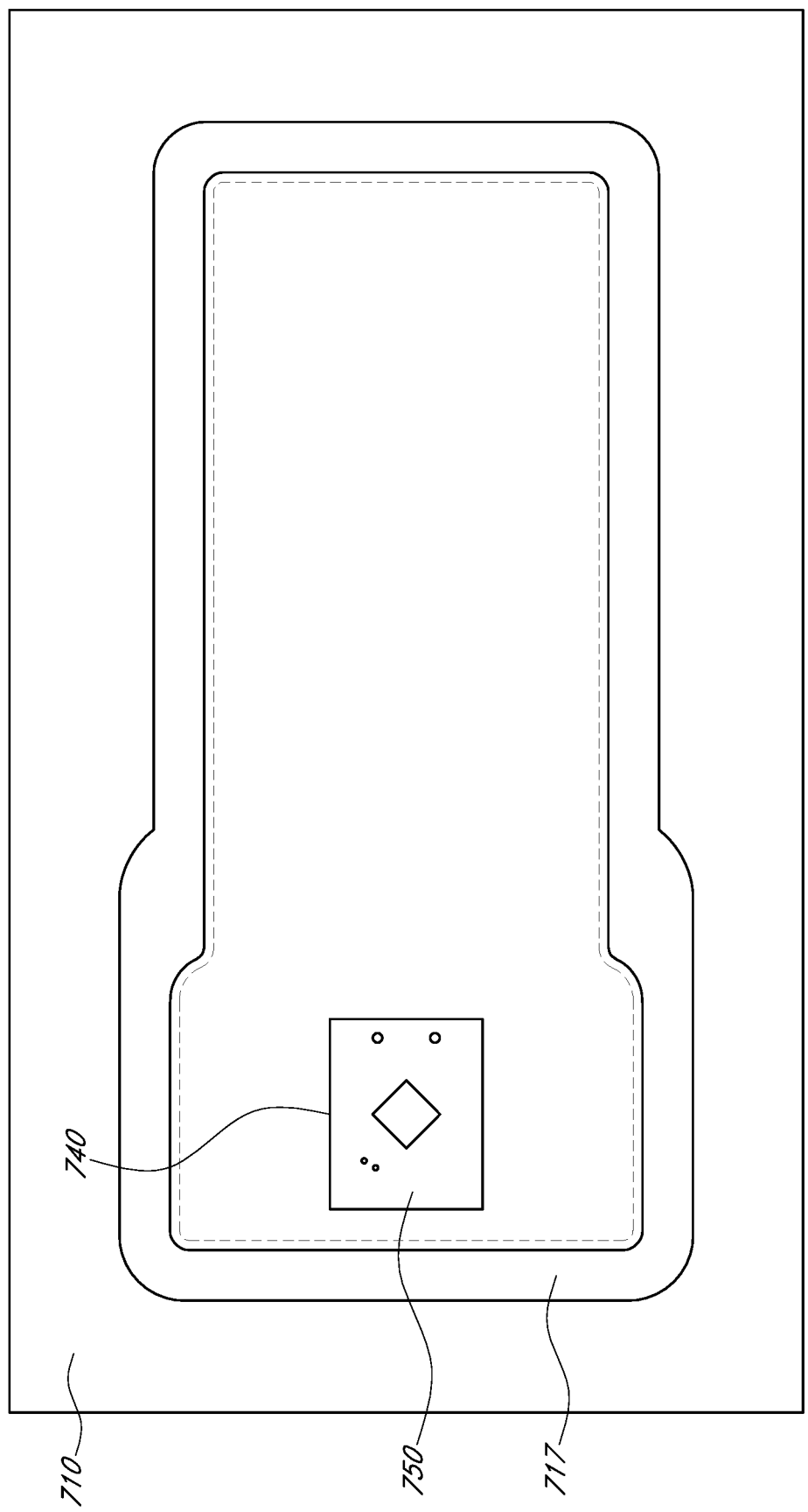

FIG. 8E illustrates an overlay layer 717 positioned over the dressing layers. The overlay layer 717 includes an opening or aperture 740 positioned over a portion of the electronics unit 750. The aperture 740 can allow for access to the switch, pump outlet components, and visual indicators on the top surface of the electronics unit 750.

Figure 8F:
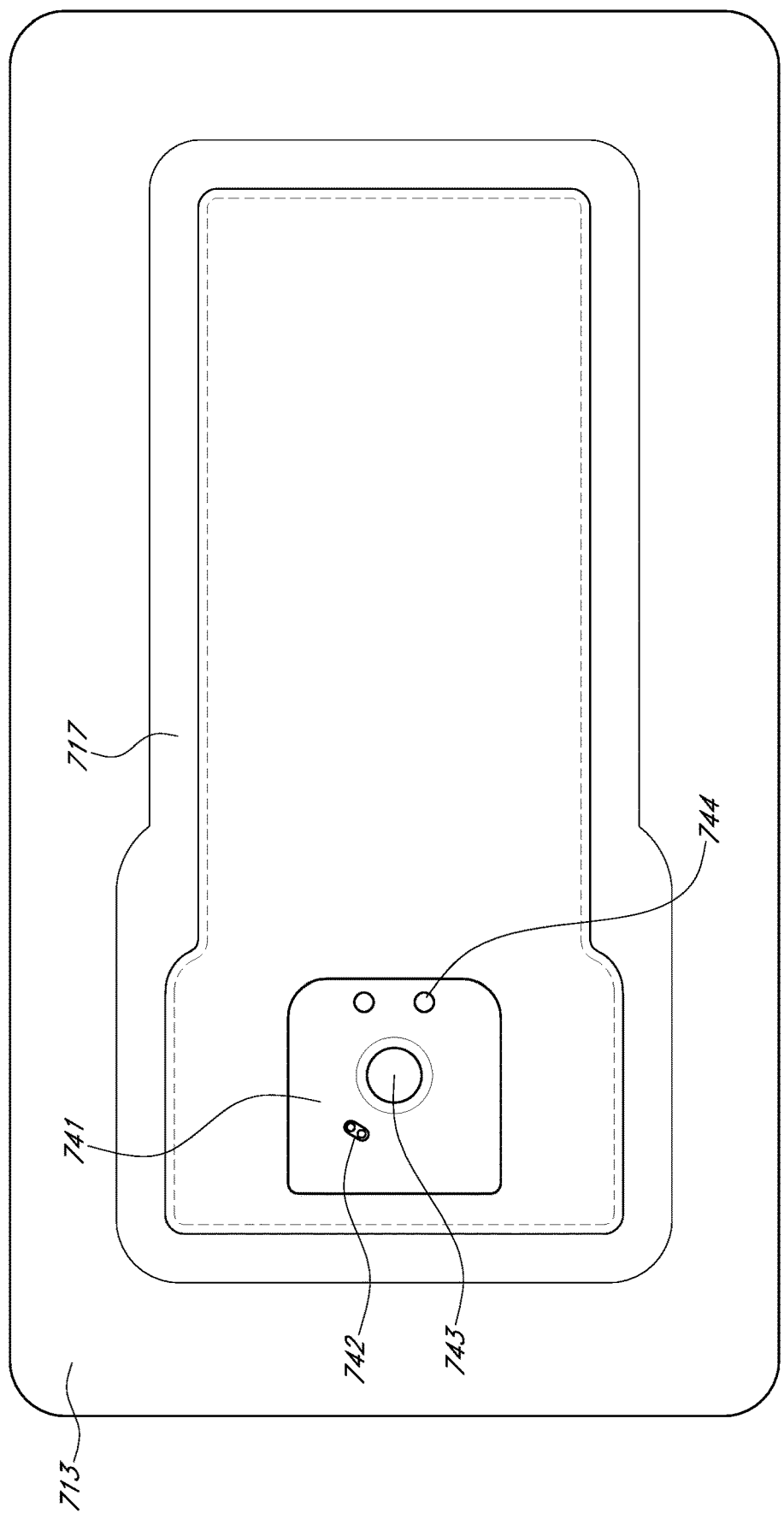

A label or covering 741 can be positioned over and cover the electronics and an opening 740 in the overlay layer 717 as shown in FIG. 8F. FIG. 8F shows a cover layer 713 covering the overlay layer 717 and electronics covering 741 and underlying dressing and electronics components. The cover layer 713 can seal to the wound contact layer 710 (shown in FIG. 8C-8E) at a perimeter region of the wound contact layer 710. In some embodiments, the label or electronics covering 741 can be positioned over the cover layer 713. In some embodiments, the cover layer 713 can seal over the electronics covering 741. In some embodiments, the electronics covering 741 can include a switch cover 743, one or more visual indicators 744, and/or pump outlet vent(s) 742 as shown in FIG. 8F. In some embodiments, the cover layer 713 can include one or more holes in the cover layer 713 positioned over the switch and/or pump outlet vent(s). In some embodiments, the cover layer 713 can include a single hole that is positioned over the switch cover 743, visual indicators 744, and/or pump outlet vent(s) 742 in the covering or label 741 as shown in FIG. 8F. In some embodiments, the label can include embossed features for the switch cover 743. In some embodiments, the embossed features of the switch cover 743 can prevent accidental activation or deactivation of the device. In some embodiments, the switch or switch cover 743 can include a tab on the switch to prevent accidental activation or deactivation.

The visual indicators 744 can provide an indication of operation of the negative pressure source and/or an indication of the level of negative pressure that is applied to the wound. In some embodiments, the visual indicators can include one or more light sources or LEDs. In some embodiments, the visual indicator light sources an illuminate to indicate a condition or change of condition. In some embodiments, the light source can illuminate in a particular sequence and/or color that indicates a condition. For example, in some embodiments, the light source can flash to notify the user that the device is operating properly. In some embodiments, the light source can automatically flash periodically and/or the light source can be activated by the switch or other button to light up and indicate a condition.

In some embodiments, the switch can be pressed and/or held down to power the dressing and electronics on and off. In some embodiments, once the switch is activated and the pump and associated colored LED, for example, green colored LED, can be used to conformed the dressing and integrated negative pressure source is operational. In some embodiments, during operation of the pump and dressing, the pump and dressing can enter the fault state indicated by a colored LED, for example, orange colored LED.

The electronics components can be incorporated in the dressing. For example, the dressing components can be assembled to form one integrated negative pressure dressing to be positioned over a wound. The following assembly description describes an embodiment of the assembly of an integrated wound dressing. In some embodiments, some or all of the assembly process can be automated and/or any or all of the processes or procedures can be done in any order.

A transmission layer can be positioned over the wound contact layer as shown in FIG. 8A. In some embodiments, the transmission layer can be positioned with the larger pores facing upward or away from the wound. FIG. 8B illustrates a bottom view of some of the components of the wound dressing to illustrate the electronic components embedded within or fit into the apertures of the large apertured pad or absorbent layer and small apertured pad or absorbent layer. In FIG. 8B, the electronics assembly is positioned switch side down. FIG. 8C illustrates the top view of the electronics assembly within the apertured pads or absorbent material placed directly on top of the transmission layer as shown in FIGS. 8C and 8D. The switch can be positioned on the top surface of the printed circuit board as shown in FIGS. 8C and 8D.

The overlay layer 717 can be positioned over the apertured pads or absorbent material with the aperture in the overlay layer positioned over the switch of the electronics assembly. In some embodiments, the edges and/or the outer perimeter of the overlay layer 717 can be adhered or secured to the top or upper surface of the wound contact layer 710. A top film or cover layer can be placed over the overlay layer 717 as shown in FIG. 8F. In some embodiments, the perimeter of the cover layer can be secured to the top or upper surface of the wound contact layer 710. In some embodiments, if the cover layer is positioned over the printed circuit board, holes can be punctured in the top film at the location of the two exhaust ports. In other embodiments, the cover layer can be provided with one or more apertures that are placed over the two exhaust ports and/or other components of the electronics unit.

A label cover can be applied over the switch and/or other components of the electronics assembly that are exposed through the apertures of the overlay layer 717 and the cover layer. The indicator portions can include transparent portions or LED windows aligned with the LED's on the PCB when the label cover is applied. In some embodiments, the LED windows can include apertures in the label cover. In other embodiments, the LED windows can be transparent portions of the label cover. The exhaust holes can also be aligned with apertures in the label cover.

Figure 9:
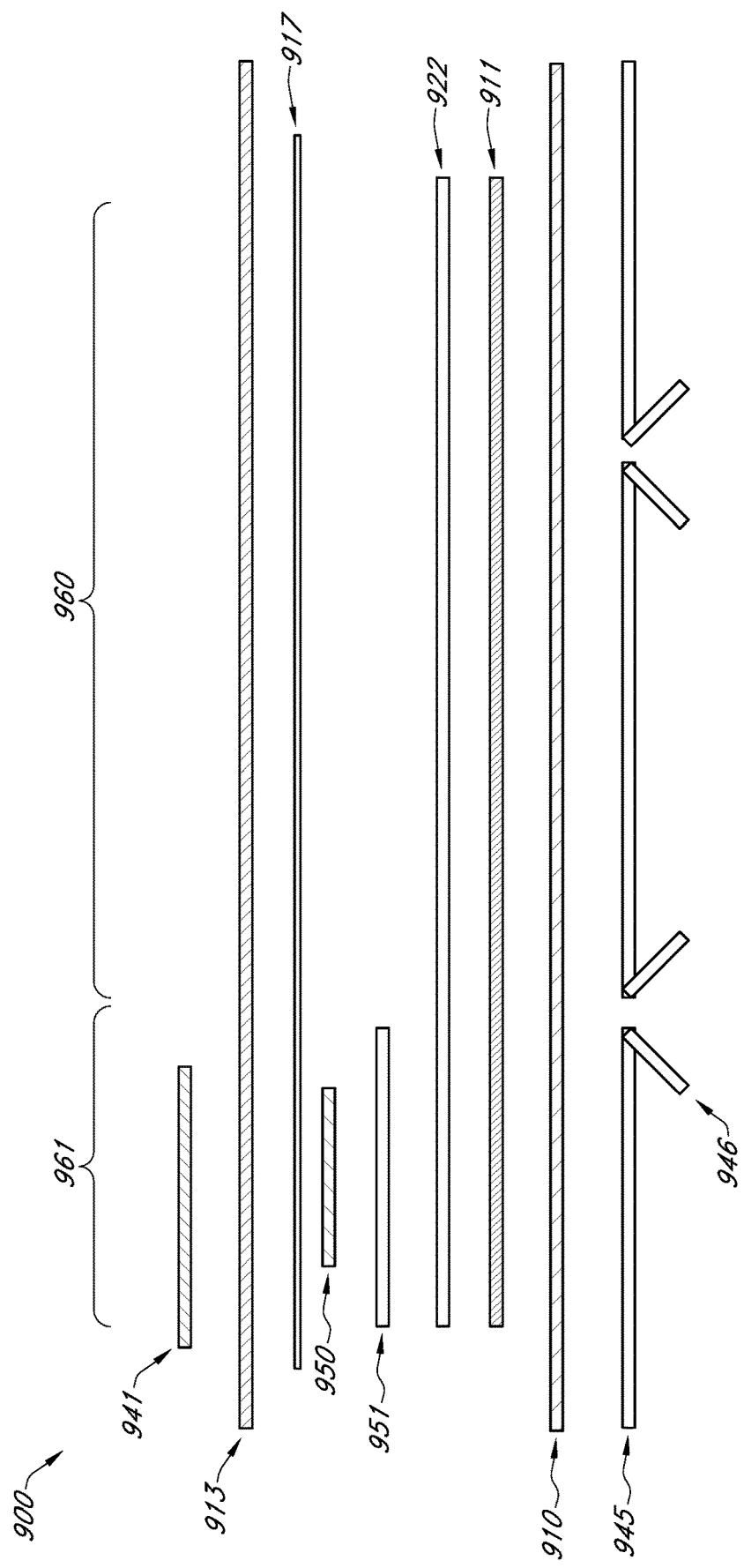
FIG. 9 illustrates a cross sectional layout of the material layers of the wound dressing incorporating an electronics assembly within the dressing

FIG. 9 illustrates a cross sectional layout of the material layers of the wound dressing incorporating an electronics assembly within the dressing. The dressing 900 included multiple material layers and an electronics assembly 950. The wound dressing 900 can include an electronics area 961 including the electronics and an absorbent area or dressing area 960 that is intended to be applied to the wound as described with reference to FIGS. 1A-1B. As described herein, the one or more of the material layers can extend into both the electronics area 961 and the dressing area 960. The dressing 900 can include a wound contact layer 910, transmission layer 911, absorbent layers 922 and 951, an overlay layer, and a cover or backing layer 913 as illustrated in FIG. 9. The absorbent layers 922 and 951 can include recesses or cutouts to receive the components of the electronics assembly 950 as described herein. In some embodiments, the overlay layer 917 and/or the cover layer 913 can include a cut out over the switch and/or indicators of the electronics assembly 950. A label or covering 941 can be positioned to cover at least a portion of the electronics assembly 950 and any cutouts in the overlay layer 917 and/or the cover layer 913. The label or covering 941 can be similar to the label or covering 741 as described previously with reference to FIGS. 6 and 8F.

Before use, the dressing can include a delivery layer 945 adhered to the bottom surface of the wound contact layer. The delivery layer 945 can cover adhesive or apertures on the bottom surface of the wound contact layer 910. In some embodiments, the delivery layer 945 can provided support for the dressing and can assist in sterile and appropriate placement of the dressing over the wound and skin of the patient. The delivery layer 945 can include handles 946 that can be used by the user to separate the delivery layer 945 from the wound contact layer 910 before applying the dressing 900 to a wound and skin of a patient.

The wound dressing with embedded electronics can be any shape or size to accommodate various types of wounds. For example, the wound dressing with embedded electronics can have a rectangular, rounded rectangular, square, T shaped, or any other shape or design. In some embodiments, the wound dressings with embedded electronics described herein can be rectangular or rounded rectangular shaped as illustrated with reference to FIGS. 1A-2B. In other embodiments, the wound dressings with embedded electronics described herein can be a T shaped as illustrated with reference to FIGS. 4A-8F.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A wound dressing apparatus comprising:
   a wound contact layer comprising a proximal wound-facing face and a distal face, wherein the proximal wound-facing face is configured to be positioned in contact with a wound;
   a spacer layer comprising a proximal wound-facing face and a distal face, the spacer layer positioned over the distal face of the wound contact layer;
   a first absorbent layer positioned on the distal face of the spacer layer, the first absorbent layer comprising a proximal wound-facing face and a distal face;
   a second absorbent layer positioned on the distal face of the first absorbent layer;
   an electronics unit comprising a negative pressure source and a negative pressure source exhaust, wherein the negative pressure source exhaust comprises a component formed to fit around an outlet side of the negative pressure source, wherein the negative pressure source exhaust is attached to an outlet of the negative pressure source and extends to an upper surface of the electronics unit;
   wherein the first and second absorbent layers comprise a recess configured to receive the electronics unit and the first and second absorbent layers are configured to be in fluid communication with the negative pressure source; and
   a cover layer comprising an aperture and an electronics covering configured to cover the aperture in the cover layer, wherein the cover layer and the electronics covering are configured to cover and form a seal over the wound contact layer, the spacer layer, the first and second absorbent layers, and the electronics unit;
   wherein the electronics covering comprises an aperture over the negative pressure source exhaust.

2. The wound dressing apparatus of claim 1, wherein the electronics unit further comprises electronic components, wherein the electronic components comprise one or more of a power source, a flexible circuit board, a sensor, a switch, and/or a light or LED indicator.

3. The wound dressing apparatus of claim 1, further comprising a negative pressure source inlet protection mechanism.

4. The wound dressing apparatus of claim 1, wherein the negative pressure source outlet or exhaust comprises an antibacterial membrane and/or a non- return valve.

5. The wound dressing apparatus of claim 3, wherein the negative pressure source inlet protection mechanism comprises a hydrophobic material configured to prevent fluid from entering the negative pressure source.

6. The wound dressing apparatus of claim 1, wherein the electronics covering comprises a switch cover.

7. The wound dressing apparatus of claim 6, wherein the switch cover is configured to allow the user to communicate with a switch to activate or deactivate the negative pressure source.

8. The wound dressing apparatus of claim 6, wherein the switch cover comprises embossed features configured to prevent accidental activation or deactivation of the negative pressure source.

9. The wound dressing apparatus of claim 6, wherein the switch cover or a switch comprises a tab to prevent activation or deactivation.

10. The wound dressing apparatus of claim 1, wherein the electronics covering comprises one or more visual indicator windows.

11. The wound dressing apparatus of claim 10, wherein the one or more visual indicator windows are configured to provide an indication of operation of the negative pressure source and/or an indication of the level of negative pressure that is applied to the wound.

12. The wound dressing apparatus of claim 10, wherein the one or more visual indicator windows comprise a transparent portion of the electronics covering.

13. The wound dressing apparatus of claim 1, wherein the electronics covering is sealed to the cover layer around the perimeter of the electronics covering.

14. The wound dressing apparatus of claim 1, wherein the electronics unit is surrounded by a material to enclose or encapsulate the negative pressure source.

15. The wound dressing apparatus of claim 1, wherein the aperture in the electronics covering is located directly over the negative pressure source exhaust.

16. A wound dressing apparatus comprising:
    a wound contact layer comprising a proximal wound-facing face and a distal face, wherein the proximal wound-facing face is configured to be positioned in contact with a wound;
    an absorbent layer, the absorbent layer comprising a proximal wound-facing face and a distal face;
    an electronics unit comprising a negative pressure source and a negative pressure source exhaust, wherein the negative pressure source exhaust comprises a component formed to fit around an outlet side of the negative pressure source, wherein the negative pressure source exhaust is attached to an outlet of the negative pressure source and extends to an upper surface of the electronics unit;
    wherein the absorbent layer comprises a recess configured to receive the electronics unit and the absorbent layer is configured to be in fluid communication with the negative pressure source; and
    a cover layer configured to cover and form a seal over the wound contact layer, the absorbent layer, and the electronics unit;
    wherein the cover layer comprises an aperture over the negative pressure source exhaust configured to allow the negative pressure source to exhaust through the aperture in the cover layer.

* * * * *